(12) United States Patent
Murphy et al.

(10) Patent No.: US 9,683,213 B2
(45) Date of Patent: Jun. 20, 2017

(54) HYDROGEL COMPOSITIONS FOR USE IN CELL EXPANSION AND DIFFERENTIATION

(71) Applicant: Wisconsin Alumni Research Foundation, Madison, WI (US)

(72) Inventors: William L. Murphy, Waunakee, WI (US); Matthew Brian Parlato, Madison, WI (US); James A Molenda, Madison, WI (US); Ngoc Nhi Le, Norcross, GA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/684,120

(22) Filed: Apr. 10, 2015

(65) Prior Publication Data
US 2015/0291930 A1    Oct. 15, 2015

Related U.S. Application Data

(60) Provisional application No. 61/978,032, filed on Apr. 10, 2014.

(51) Int. Cl.
| | | |
|---|---|---|
| *C12N 5/0735* | (2010.01) | |
| *G01N 33/483* | (2006.01) | |
| *B01J 19/00* | (2006.01) | |
| *G01N 21/64* | (2006.01) | |

(52) U.S. Cl.
CPC ....... *C12N 5/0606* (2013.01); *G01N 33/4833* (2013.01); *B01J 19/0046* (2013.01); *B01J 2219/00596* (2013.01); *C12N 2533/20* (2013.01); *C12N 2533/30* (2013.01); *C12N 2537/10* (2013.01); *G01N 21/6452* (2013.01); *G01N 2610/00* (2013.01)

(58) Field of Classification Search
CPC .......................... C12N 5/0606; C12N 2533/30
USPC ........................................... 514/1.1; 435/325
See application file for complete search history.

(56) References Cited

U.S. PATENT DOCUMENTS

| | | |
|---|---|---|
| 2005/0019843 A1 | 1/2005 | Chen et al. |
| 2012/0149781 A1 | 6/2012 | Lee et al. |
| 2012/0225814 A1 | 9/2012 | Hanjay-Putra et al. |
| 2013/0210147 A1 | 8/2013 | Jeannin et al. |
| 2013/0260464 A1 | 10/2013 | Vannier et al. |
| 2013/0296177 A1 | 11/2013 | Koepsel et al. |
| 2014/0017284 A1 | 1/2014 | Yang et al. |
| 2014/0018263 A1 | 1/2014 | Levkin et al. |
| 2015/0104812 A1 | 4/2015 | Grevesse et al. |

OTHER PUBLICATIONS

Fairbanks (Advanced Materials 21, 5005-5010, 2009).*
Porter A M (American Journal of Physiology. Cell Physiology 301(5), C1086-92 (2011).*
Liu, Zongbin (Biomicrofluidics 6(2), p. 24111-1 to p. 24111-12, 2012).*
Hern, et al., Incorporation of adhesion peptides into nonadhesive hydrogels useful for tissue resurfacing, pp. 266-279, 1998.
Shih, et al., Cross-Linking and Degradation of Step-Groth Hydrogels Formed by Thiol-Ene Photoclick Chemistry, Bio Macromolecules, 2012, pp. 2003-2012.
Pishko, Michael V., Microfabricated Cell-based biosensor Arrays, Engineering in Medicine and Biology 27th Annual Conference, Shanghai, China, Sep. 1-4, 2005.
Kyburz et al., Three-dimensional hMSC motility within peptide-functionalized PEG-based hydrogels of varying adhesivity and crosslinking density, Acta Biomaterialia, vol. 9, No. 5, pp. 6381-6392, 2013.
Leslie-Barbick et al., The promotion of microvasculature formation in poly(ethylene glycol) diacrylate hydrogels by an immobilized VEGF-mimetic peptide, Biomaterials, vol. 32, No. 25, pp. 5782-5789, 2011.
Love et al., Self-Assembled Monolayers of Thiolates on Metals as a Form of Nanotechnology, Chem. Rev. 2005, 105:1103-1169.
Strother et al., Synthesis and Characterization of DNA-Modified Silicon (III) Surfaces, J. Am. Chem. Soc. 2000, 122:1205-1209.
Schwartz et al., Chemical modification of silicon surfaces for biological applications, 2005 Phys. Stat. Sol. (a) 202 (8):1380-1384.
Strother et al., Photochemical Functionalization of Diamond Films, Langmuir, 2002, 18:968-971.
Polizzotti et al., Three-Dimensional Biochemical Patterning of Click-Based Composit Hydrogels via Thiolene Photopolymerization, Biomacromolecules 2008, 9:1084-1087.
Fairbanks et al., A Versatile Synthetic Extracellular Matrix Mimic via Thiol-Norbornene Photopolymerization, Adv. Mater. 2009, 21:5005-5010.
Nagase and Fields, Human Matrix Metalloproteinase Specificity Studies Using Collagen Sequence-Based Synthetic Peptides, Biopolymers 1996, 40:399-416.
Toepke et al., Characterization of Thiol-Ene Crosslinked PEG Hydrogels, 2013, Macromol. Mater. Eng., 298:699-703.
Impellitteri et al., Specific VEGF sequestering and release using peptide-functionalized hydrogel microspheres, Biomaterials 2012, 33:3475-84.
Belair and Murphy, Specific VEGF sequestering to biomaterials: Influence of serum stability, Acta Biomater, 2013.
Gould et al., Small Peptide Functionalized Thiol-Ene Hydrogels as Culture Substrates for Understanding Valvular Interstitial Cell Activation and de novo Tissue Deposition, Acta Biomater 2012, 8:3201-3209.
Seo et al., Attachment of hydrogel microstructures and proteins to glass via thiol-terminated silanes, Colloids Surf B Biointerfaces 2012, 98:1-6.
Halliwell et al., A Factorial Analysis of Silanization Conditions for the Immobilization of Oligonucletotides on Glass Surfaces, Anal Chem 2001, 73:2476-2483.
Cras et al., Comparison of chemical cleaning methods of glass in preparation for silanization, Biosens Bioelectron 1999, 14:683-688.
Vistas et al., Silanization of glass chips-A factorial approach for optimization, Appl Surf Sci 2013, 286:314-318.
Jo et al., Three-Dimensional Micro-Channel Fabrication in Polydimethylsiloxane (PDMS) Elastomer, 2000 J Microelectromechanical Syst. 9:76-81.

(Continued)

*Primary Examiner* — David Lukton
(74) *Attorney, Agent, or Firm* — Stinson Leonard Street LLP

(57) ABSTRACT

Hydrogel compositions and methods of using hydrogel compositions are disclosed. Advantageously, the hydrogel compositions offer the ability to promote cellular expansion and/or cellular differentiation of various cells.

19 Claims, 10 Drawing Sheets
(1 of 10 Drawing Sheet(s) Filed in Color)

(56) References Cited

OTHER PUBLICATIONS

Prime and Whitesides, Adsorption of Proteins onto Surfaces Containing End-Attached Oligo(ethylene oxide): A Model System Using Self-Assembled Monolayers, 1993 J. Am. Chem. Soc. 115:10714-10721.
Engler et al., Matrix Elasticity Directs Stem Cell Lineage Specification, Cell 126:677 (2006).
Nguyen et al. "Differential effects of cell adhesion, modulus and VEGFR-2 inhibition on capillary network formation in synthetic hydrogel arrays," Biomaterials, 35, 2014, pp. 2149-2161.
Hansen et al., "Biomaterial arrays with defined adhesion ligand densities and matrix stiffness identify distinct phenotypes for tumorigenic and non-tumorigenic human mesenchymal cell types," Biomaterials Science, Royal Society of Chemistry, Published Jan. 22, 2014, 12 pages.
Raza, Asad et al., 'The influence of matrix degradation and functionality on cell survival and morphogenesis in PEG-based hydrogels', Macromolecular Bioscience, 2013, vol. 13, No. 8, pp. 1048-1058.
Banerjee, Akhilesh et al., 'The influence of hydrogel modulus on the proliferation and differentiation of encapsulated neural stem cells', Biomaterials, 2009, vol. 30, No. 27, pp. 4695-4699.

\* cited by examiner

SEQUENCE LISTING

```
<160> NUMBER OF SEQ ID NOS: 48

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Arg Gly Asp Ser
1

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Cys Arg Gly Asp Ser
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Gly Arg Gly Asp Ser Pro
1               5

<210> SEQ ID NO 4
<211> LENGTH: 5
<212> TYPE: PRT
<213> ORGANISM: Artificial Sequence
```

```
<220> FEATURE:
<223> OTHER INFORMATION: Synthetic

<400> SEQUENCE: 4

Pro His Ser Arg Asn
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Gly Trp Gly Gly Arg Gly Asp Ser Pro
1               5

<210> SEQ ID NO 6
<211> LENGTH: 13
<212> TYPE: PRT
<213> ORGANISM: Artificial Sequence
<220> FEATURE:
<223> OTHER INFORMATION: Synthetic

<400> SEQUENCE: 6

Ser Ile Asp Gln Val Glu Pro Tyr Ser Ser Thr Ala Gln
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic

<400> SEQUENCE: 7

Gly Arg Asn Ile Ala Glu Ile Ile Lys Asp Ile
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Asp Ile Thr Tyr Val Arg Leu Lys Phe
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Asp Ile Thr Val Thr Leu Asn Arg Leu
1               5

<210> SEQ ID NO 10
<211> LENGTH: 8
<212> TYPE: PRT
<213> ORGANISM: Artificial Sequence
<220> FEATURE:
```

<223> OTHER INFORMATION: Synthetic

<400> SEQUENCE: 10

Gly Arg Tyr Val Val Leu Pro Arg
1               5

<210> SEQ ID NO 11
<211> LENGTH: 13
<212> TYPE: PRT
<213> ORGANISM: Artificial Sequence
<220> FEATURE:
<223> OTHER INFORMATION: Synthetic

<400> SEQUENCE: 11

Gly Asn Arg Trp His Ser Ile Tyr Ile Thr Arg Phe Gly
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic

<400> SEQUENCE: 12

Gly Ala Ser Ile Lys Val Ala Val Ser Ala Asp Arg
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Synthetic

<400> SEQUENCE: 13

Gly Thr Thr Val Lys Tyr Ile Phe Arg
1               5

<210> SEQ ID NO 14
<211> LENGTH: 10
<212> TYPE: PRT
<213> ORGANISM: Artificial Sequence
<220> FEATURE:
<223> OTHER INFORMATION: Synthetic

<400> SEQUENCE: 14

Gly Ser Ile Lys Ile Arg Gly Thr Tyr Ser
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic

<400> SEQUENCE: 15

Gly Ser Ile Asn Asn Asn Arg
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic

```
<400> SEQUENCE: 16

Ser Asp Pro Gly Tyr Ile Gly Ser Arg
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic

<400> SEQUENCE: 17

Tyr Ile Gly Ser Arg
1               5

<210> SEQ ID NO 18
<211> LENGTH: 14
<212> TYPE: PRT
<213> ORGANISM: Artificial Sequence
<220> FEATURE:
<223> OTHER INFORMATION: Synthetic

<400> SEQUENCE: 18

Gly Thr Pro Gly Pro Gln Gly Ile Ala Gly Gln Gly Val Val
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Synthetic

<400> SEQUENCE: 19

Gly Thr Pro Gly Pro Gln Gly Ile Ala Gly Gln Arg Val Val
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Synthetic

<400> SEQUENCE: 20

Met Asn Tyr Tyr Ser Asn Ser
1               5

<210> SEQ ID NO 21
<211> LENGTH: 12
<212> TYPE: PRT
<213> ORGANISM: Artificial Sequence
<220> FEATURE:
<223> OTHER INFORMATION: Synthetic

<400> SEQUENCE: 21

Lys Lys Gln Arg Phe Arg His Arg Asn Arg Lys Gly
1               5                   10

<210> SEQ ID NO 22
<211> LENGTH: 18
<212> TYPE: PRT
<213> ORGANISM: Artificial Sequence
<220> FEATURE:
<223> OTHER INFORMATION: Synthetic
```

```
<400> SEQUENCE: 22

Gly Gly Gly Lys Leu Thr Trp Gln Glu Leu Tyr Gln Leu Lys Tyr Lys
1               5                   10                  15

Gly Ile

<210> SEQ ID NO 23
<211> LENGTH: 15
<212> TYPE: PRT
<213> ORGANISM: Artificial Sequence
<220> FEATURE:
<223> OTHER INFORMATION: Synthetic

<400> SEQUENCE: 23

Lys Leu Thr Trp Gln Glu Leu Tyr Gln Leu Lys Tyr Lys Gly Ile
1               5                   10                  15

<210> SEQ ID NO 24
<211> LENGTH: 12
<212> TYPE: PRT
<213> ORGANISM: Artificial Sequence
<220> FEATURE:
<223> OTHER INFORMATION: Synthetic

<400> SEQUENCE: 24

Lys Ile Pro Lys Ala Ser Ser Val Pro Thr Glu Leu
1               5                   10

<210> SEQ ID NO 25
<211> LENGTH: 20
<212> TYPE: PRT
<213> ORGANISM: Artificial Sequence
<220> FEATURE:
<223> OTHER INFORMATION: Synthetic

<400> SEQUENCE: 25

Lys Ile Pro Lys Ala Ser Ser Val Pro Thr Glu Leu Ser Ala Ile Ser
1               5                   10                  15

Thr Leu Tyr Leu
            20

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Lys Arg Thr Gly Gln Tyr Lys Leu
1               5

<210> SEQ ID NO 27
<211> LENGTH: 14
<212> TYPE: PRT
<213> ORGANISM: Artificial Sequence
<220> FEATURE:
<223> OTHER INFORMATION: Synthetic

<400> SEQUENCE: 27

Lys Cys Gly Gly Pro Gln Gly Ile Trp Gly Gln Gly Cys Lys
1               5                   10

<210> SEQ ID NO 28
<211> LENGTH: 14
<212> TYPE: PRT
```

```
<213> ORGANISM: Artificial Sequence
<220> FEATURE:
<223> OTHER INFORMATION: Synthetic

<400> SEQUENCE: 28

Lys Cys Gly Gly Pro Gln Gly Ile Ala Gly Gln Gly Cys Lys
1               5                   10

<210> SEQ ID NO 29
<211> LENGTH: 22
<212> TYPE: PRT
<213> ORGANISM: Artificial Sequence
<220> FEATURE:
<223> OTHER INFORMATION: Synthetic

<400> SEQUENCE: 29

Cys Arg Gly Asp Gly Gly Gly Gly Gly Gly Gly Gly Gly Gly
1               5                   10                  15

Gly Pro His Ser Arg Asn
            20

<210> SEQ ID NO 30
<211> LENGTH: 19
<212> TYPE: PRT
<213> ORGANISM: Artificial Sequence
<220> FEATURE:
<223> OTHER INFORMATION: Synthetic

<400> SEQUENCE: 30

Cys Pro His Ser Arg Asn Ser Gly Ser Gly Ser Gly Ser Gly
1               5                   10                  15

Arg Gly Asp

<210> SEQ ID NO 31
<211> LENGTH: 10
<212> TYPE: PRT
<213> ORGANISM: Artificial Sequence
<220> FEATURE:
<223> OTHER INFORMATION: Synthetic

<400> SEQUENCE: 31

Gly Cys Tyr Gly Arg Gly Asp Ser Pro Gly
1               5                   10

<210> SEQ ID NO 32
<211> LENGTH: 5
<212> TYPE: PRT
<213> ORGANISM: Artificial Sequence
<220> FEATURE:
<223> OTHER INFORMATION: Synthetic

<400> SEQUENCE: 32

Cys Arg Asp Gly Ser
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: D-phenylalanine

<400> SEQUENCE: 33
```

```
Arg Gly Asp Phe Cys
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic

<400> SEQUENCE: 34

Arg Gly Asp Pro His Ser Arg Asn
1               5

<210> SEQ ID NO 35
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: D-phenylalanine
<220> FEATURE:
<221> NAME/KEY: MISC_FEATURE
<222> LOCATION: (4)..(4)
<223> OTHER INFORMATION: D-alanine
<220> FEATURE:
<221> NAME/KEY: MISC_FEATURE
<222> LOCATION: (5)..(5)
<223> OTHER INFORMATION: D-tyrosine
<220> FEATURE:
<221> NAME/KEY: MISC_FEATURE
<222> LOCATION: (6)..(6)
<223> OTHER INFORMATION: D-leucine

<400> SEQUENCE: 35

Cys Glu Phe Ala Tyr Leu Ile Asp Phe Asn Trp Glu Tyr Pro Ala Ser
1               5                   10                  15

Lys

<210> SEQ ID NO 36
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: D-alanine
<220> FEATURE:
<221> NAME/KEY: MISC_FEATURE
<222> LOCATION: (7)..(7)
<223> OTHER INFORMATION: D-phenylalanine
<220> FEATURE:
<221> NAME/KEY: MISC_FEATURE
<222> LOCATION: (13)..(13)
<223> OTHER INFORMATION: D-tyrosine
<220> FEATURE:
<221> NAME/KEY: MISC_FEATURE
<222> LOCATION: (17)..(17)
<223> OTHER INFORMATION: D-leucine

<400> SEQUENCE: 36

Cys Asp Ala Pro Tyr Asn Phe Glu Phe Ala Trp Glu Tyr Val Ile Ser
1               5                   10                  15

Leu Lys
```

<210> SEQ ID NO 37
<211> LENGTH: 12
<212> TYPE: PRT
<213> ORGANISM: Artificial Sequence
<220> FEATURE:
<223> OTHER INFORMATION: Synthetic

<400> SEQUENCE: 37

Arg Lys Arg Leu Gln Val Gln Leu Ser Ile Arg Thr
1               5                   10

<210> SEQ ID NO 38
<211> LENGTH: 5
<212> TYPE: PRT
<213> ORGANISM: Artificial Sequence
<220> FEATURE:
<223> OTHER INFORMATION: Synthetic

<400> SEQUENCE: 38

Ile Lys Val Ala Val
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic

<400> SEQUENCE: 39

Tyr Ile Gly Ser Arg
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic

<400> SEQUENCE: 40

Lys Arg Thr Gly Gln Tyr Lys Leu
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic

<400> SEQUENCE: 41

Thr Tyr Arg Ser Arg Lys Tyr
1               5

<210> SEQ ID NO 42
<211> LENGTH: 17
<212> TYPE: PRT
<213> ORGANISM: Artificial Sequence
<220> FEATURE:
<223> OTHER INFORMATION: Synthetic

<400> SEQUENCE: 42

Lys Arg Thr Gly Gln Tyr Lys Leu Gly Ser Lys Thr Gly Pro Gly Gln
1               5                   10                  15

Lys

<210> SEQ ID NO 43
<211> LENGTH: 14
<212> TYPE: PRT
<213> ORGANISM: Artificial Sequence
<220> FEATURE:
<223> OTHER INFORMATION: Synthetic

<400> SEQUENCE: 43

Gln Ala Lys His Lys Gln Arg Lys Arg Leu Lys Ser Ser Cys
1               5                   10

<210> SEQ ID NO 44
<211> LENGTH: 17
<212> TYPE: PRT
<213> ORGANISM: Artificial Sequence
<220> FEATURE:
<223> OTHER INFORMATION: Synthetic

<400> SEQUENCE: 44

Ser Pro Lys His His Ser Gln Arg Ala Arg Lys Lys Asn Lys Asn
1               5                   10                  15

Cys

<210> SEQ ID NO 45
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is a hydropathic residue
<220> FEATURE:
<221> NAME/KEY: MISC_FEATURE
<222> LOCATION: (2)..(2)
<223> OTHER INFORMATION: B is a basic residue
<220> FEATURE:
<221> NAME/KEY: MISC_FEATURE
<222> LOCATION: (3)..(3)
<223> OTHER INFORMATION: B is a basic residue
<220> FEATURE:
<221> NAME/KEY: MISC_FEATURE
<222> LOCATION: (4)..(4)
<223> OTHER INFORMATION: X is a hydropathic residue
<220> FEATURE:
<221> NAME/KEY: MISC_FEATURE
<222> LOCATION: (5)..(5)
<223> OTHER INFORMATION: B is a basic residue
<220> FEATURE:
<221> NAME/KEY: MISC_FEATURE
<222> LOCATION: (6)..(6)
<223> OTHER INFORMATION: X is a hydropathic residue

<400> SEQUENCE: 45

Xaa Asx Asx Xaa Asx Xaa
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is a hydropathic residue
<220> FEATURE:
<221> NAME/KEY: MISC_FEATURE

```
<222> LOCATION: (2)..(2)
<223> OTHER INFORMATION: B is a basic residue
<220> FEATURE:
<221> NAME/KEY: MISC_FEATURE
<222> LOCATION: (3)..(3)
<223> OTHER INFORMATION: B is a basic residue
<220> FEATURE:
<221> NAME/KEY: MISC_FEATURE
<222> LOCATION: (4)..(4)
<223> OTHER INFORMATION: B is a basic residue
<220> FEATURE:
<221> NAME/KEY: MISC_FEATURE
<222> LOCATION: (5)..(5)
<223> OTHER INFORMATION: X is a hydropathic residue
<220> FEATURE:
<221> NAME/KEY: MISC_FEATURE
<222> LOCATION: (6)..(6)
<223> OTHER INFORMATION: X is a hydropathic residue
<220> FEATURE:
<221> NAME/KEY: MISC_FEATURE
<222> LOCATION: (7)..(7)
<223> OTHER INFORMATION: B is a basic residue
<220> FEATURE:
<221> NAME/KEY: MISC_FEATURE
<222> LOCATION: (8)..(8)
<223> OTHER INFORMATION: X = hydropathic residue

<400> SEQUENCE: 46

Xaa Asx Asx Asx Xaa Xaa Asx Xaa
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic

<400> SEQUENCE: 47

Arg Gly Asp Ser Pro
1               5

<210> SEQ ID NO 48
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: d-phenylalanine

<400> SEQUENCE: 48

Arg Ala Asp Phe
1
```

HYDROGEL COMPOSITIONS FOR USE IN CELL EXPANSION AND DIFFERENTIATION

CROSS-REFERENCE TO RELATED APPLICATION

This application claims priority to U.S. Provisional Patent Application No. 61/978,032, filed on Apr. 10, 2014, which is incorporated by reference herein in its entirety.

STATEMENT OF GOVERNMENT SUPPORT

This invention was made with government support under HL093282 and AR059916 awarded by the National Institutes of Health. The government has certain rights in the invention.

STATEMENT IN SUPPORT FOR FILING A SEQUENCE LISTING

A paper copy of the Sequence Listing and a computer readable form of the Sequence Listing containing the file named "P150263US01_ST25.txt", which is 11,615 bytes in size (as measured in MICROSOFT WINDOWS® EXPLORER), are provided herein and are herein incorporated by reference. This Sequence Listing consists of SEQ ID NOs:1-48.

BACKGROUND OF THE DISCLOSURE

The present disclosure relates generally to methods for preparing biomaterial compositions and methods for using the biomaterial compositions. More particularly, the present disclosure relates to hydrogel compositions and to methods for using the hydrogel compositions to promote cell expansion and cell differentiation.

The development of most tissue types involves a complex interplay of multiple signals leading to controlled precursor cell differentiation into mature, tissue-specific cell types. For example, mesenchymal stem cells (MSCs) may be differentiated in vitro into osteoblasts, chondrocytes, myoblasts, adipocytes, neurons, and endothelial cells by exposure to a variety of growth factors. Routine cellular expansion and differentiation protocols rely on high concentrations of expensive recombinant growth factors. Substantial progress has been made in the development of defined media, but only more recently has the role of substrates and cell-substrate adhesion on cell growth been examined.

Currently, tissue culture polystyrene (TCPS) is the "gold standard" for cellular expansion and differentiation during in vitro cell culture, particularly, for human mesenchymal stem cells (hMSCs); however, TCPS does not allow the user to control substrate stiffness and growth factor regulation. Stiffness has been demonstrated to be important in controlling cellular proliferation, lineage specification, commitment, and maturation.

Accordingly, there exists a need for methods for preparing biomaterial compositions that will support survival and growth of cells in culture, and particularly, to provide specific molecules that promote cellular expansion, cellular differentiation and regulate cellular behavior. It would further be advantageous if the biomaterial compositions allowed for control over both biomaterial substrate stiffness and growth factor signaling.

BRIEF DESCRIPTION OF THE DISCLOSURE

The present disclosure relates generally to biomaterial compositions and methods for using the biomaterial compositions. More particularly, the present disclosure relates to hydrogel compositions and methods for promoting cellular expansion and cellular differentiation using the hydrogel compositions.

In accordance with the present disclosure, methods for preparing hydrogel compositions to support survival and growth of cells in culture have been discovered. The hydrogel compositions of the present disclosure can also be used for two-dimensional (2D) and three-dimensional (3D) cell culture. The hydrogel compositions of the present disclosure can further be used for two-dimensional and three-dimensional enrichment of biomolecules such as, for example, biomolecules to cell surfaces using soluble factor binders. The hydrogel compositions further offer design control over both hydrogel substrate stiffness and growth factor signaling, allow for attachment with phenotypes consistent with those offered by conventional MATRIGEL®, and growth factor regulation.

In one aspect, the present disclosure is directed to a method of promoting cellular expansion. The method includes preparing a hydrogel composition, wherein the hydrogel composition includes a polyethylene glycol functionalized with norbornene, a crosslinking peptide, and a cell adhesion peptide; contacting a cell with the hydrogel composition; and culturing the cell.

In another aspect, the present disclosure is directed to a method of promoting cellular differentiation. The method includes preparing a hydrogel composition, wherein the hydrogel composition includes a polyethylene glycol functionalized with norbornene, a crosslinking peptide, and a cell adhesion peptide; contacting a cell the hydrogel composition; and culturing the cell.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The disclosure will be better understood, and features, aspects and advantages other than those set forth above will become apparent when consideration is given to the following detailed description thereof. Such detailed description makes reference to the following drawings, wherein.

Figure 1A:
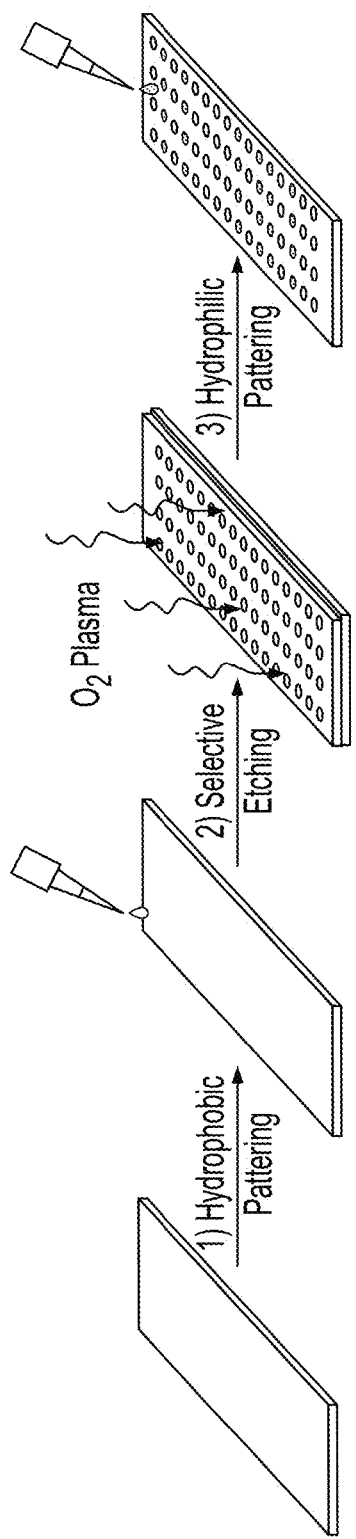
FIGS. 1A-1B are schematic illustrations of the steps for preparing a hydrogel array of the present disclosure.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the scope of the disclosure as defined by the appended claims.

DETAILED DESCRIPTION OF THE DISCLOSURE

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

In accordance with the present disclosure, methods for preparing biomaterial compositions for promoting cellular expansion and differentiation have been discovered. More particularly, the present disclosure relates to hydrogel compositions. In one aspect, hydrogel compositions can be prepared as a hydrogel array with individually controlled hydrogel spot modulus, hydrogel spot polymer density, hydrogel spot ligand identity and hydrogel spot ligand density and to methods for preparing the hydrogel arrays. In another aspect, the hydrogel compositions can be prepared as coatings such as for use on the surfaces of cell culture plates. In yet another aspect, the hydrogel compositions can be prepared as microcarriers in suspension culture. The hydrogel compositions of the present disclosure can be functionalized with biomolecules, are compatible with cell culture and are biocompatible. The hydrogel compositions of the present disclosure can be used to alter (e.g., enhance, inhibit and change) cell function, and in particular, cellular expansion, maturation and differentiation.

As known by those skilled in the art, a hydrogel composition is a network of polymer chains that are hydrophilic in which a polymeric material and water are in an equilibrated form. The hydrogel composition is formed using unpolymerized starting components. The polymeric material can be, for example, a natural polymer material, a synthetic polymer material and combinations thereof.

The methods for preparing hydrogel compositions of the present disclosure advantageously allows for the direct incorporation of peptides into the hydrogel network during polymerization by including a cysteine in the amino acid sequence during synthesis, which allows for eliminating the need for post-synthetic modifications. In this way, peptides can be utilized as crosslinkers by including cysteine on each end or they can be incorporated as pendant groups, which can be pre-coupled to the polymer backbone and mixed in varying combinations or incorporated during polymerization for simplicity.

Hydrogel Compositions and Methods for Preparing Hydrogel Compositions

The present disclosure is generally directed to methods for preparing a hydrogel composition and use of the resulting compositions. When used to prepare a hydrogel array, the preparation methods generally include contacting a hydrogel precursor solution with a substrate, wherein the substrate includes a hydrophobic region and a hydrophilic region; placing a surface-modified substrate onto the hydrogel precursor solution such that the hydrogel precursor solution is located between the substrate and the surface-modified substrate; polymerizing the hydrogel precursor solution; and separating the surface-modified substrate from the substrate, to result in the hydrogel array. (See, FIGS. 1A-1B). Thus, the polymer hydrogel precursor solution polymerizes between the substrate and the surface-modified substrate and the resultant hydrogel transfers with the surface-modified substrate such that the surface-modified substrate includes the hydrogel array. In one embodiment, the hydrogel array can be patterned to include an array of hydrogel spots surrounded by a hydrogel-free background as described in more detail below. In another embodiment, the hydrogel array can be patterned such that an array of hydrogel-free spots (or pools) is formed within a hydrogel background as described in more detail below.

Figure 5:
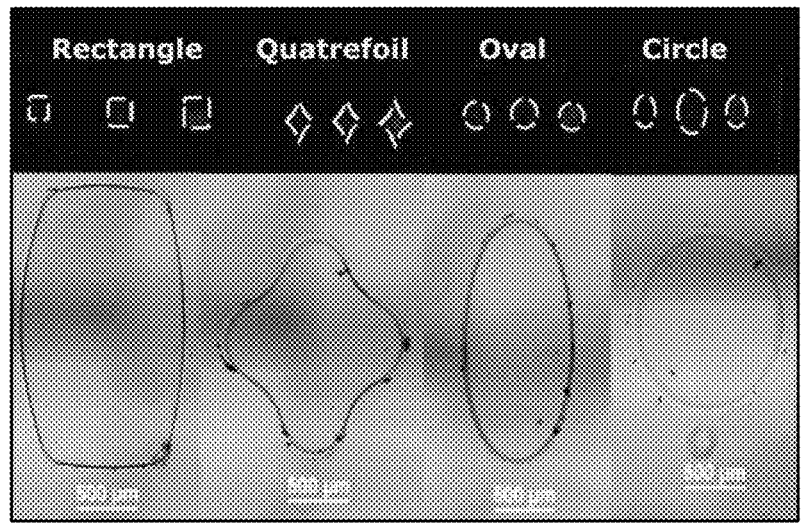
FIG. 5 illustrates high magnification top-view images showing different shapes of individual hydrogel spots.

In hydrogel arrays having hydrogel spots, the resultant hydrogel array can be patterned to result in differential wettability to define the geometry of each hydrogel spot and confine the contents of each hydrogel spot of the array, as well as define the spatial pattern of each hydrogel spot in the array in relation to neighboring spots. This is particularly useful for preparing hydrogel arrays for use with common microarray add-ons of different sizes and dimensions consistent with those of common multi-well plates (e.g., 96 well plates, 384 well plates, etc.) This is also useful for use with multichannel pipettes for enhanced-throughput cell culture, media exchange, and the like. The individual hydrogel spots of the array can have any desired shape (see e.g., FIG. 5). For example, the shape can be circular, round, oval, quatrefoil, rectangular, triangular, star-shaped, diamond-shaped, combinations thereof, and the like. Patterns of hydrogel spots may also be created in rows, spirals, circles, squares, rectangles, combinations thereof, and the like. The shape of the individual hydrogel spot can be varied by changing the pattern of the stencil used for etching during patterning of the patterned substrate.

In hydrogel arrays having hydrogel-free spots, the individual hydrogel-free spots can have any desired shape. For example, the shape can be circular, round, oval, quatrefoil, rectangular, triangular, star-shaped, diamond-shaped, combinations thereof, and the like. Patterns of hydrogel-free spots may also be created in rows, spirals, circles, squares, rectangles, combinations thereof, and the like. The shape of the individual hydrogel-free spot can be varied by changing the pattern of the stencil used for etching during patterning of the patterned substrate.

The upper size limit of the hydrogel array depends on the dimensions of the patterned substrate and/or the dimensions of the surface-modified substrate. The resultant hydrogel array can also be patterned to result in individual hydrogel spots and hydrogel-free spots having any desired sizes. The size and shape of the individual hydrogel spot and hydrogel-free spot can be varied by changing the pattern of the stencil used for etching during patterning of the patterned substrate. Suitable individual hydrogel spot size of the hydrogel array can be small enough to accommodate a single cell, but also large enough to accommodate many cells, for example. Thus, the individual hydrogel spot size of the hydrogel array can have any desired diameter. Particularly suitable individual hydrogel spot sizes of the hydrogel array can be about 10 μm and larger.

A patterned substrate can be prepared by creating hydrophobic regions and hydrophilic regions formed by self-assembled monolayers (SAMs), such as described in U.S. patent application Ser. No. 14/339,938, filed on Jul. 24, 2014, herein incorporated by reference to the extent it is consistent herewith. Suitable substrates for forming self-assembled monolayers are known to those skilled in the art and can be, for example, metal-coated substrates, silicon substrates, diamond substrates, polydimethylsiloxane (PDMS) substrates, and the like (as described in Love et al., Chem. Rev. 2005, 105:1103-1169, for example, which is hereby incorporated by reference to the extent its disclosure is consistent with the present disclosure). The patterned substrate can be prepared, for example, by forming regions with differential wettability on a substrate by immersing the substrate in a perfluorinated alkanethiol solution to allow perfluorinated alkanethiolate self-assembled monolayers (fluoraSAMs) to form. To form hydrophilic regions, a stencil can be placed on the fluoraSAMs metal-coated substrate to selectively protect regions of the fluoraSAMs metal-coated substrate from plasma etching. Exposed regions of the fluoraSAMs substrate can then be etched by oxygen plasma treatment to form etched fluoraSAMs in the substrate. The substrate is then immersed in a hydroxyl-terminated alkanethiol solution to form a hydrophilic alkanethiolate SAM ($EG_3SAM$) in the etched regions of the substrate. The resulting patterned substrate possesses differential wettability based on the hydrophobic SAMs and hydrophilic SAMs.

Figure 4:
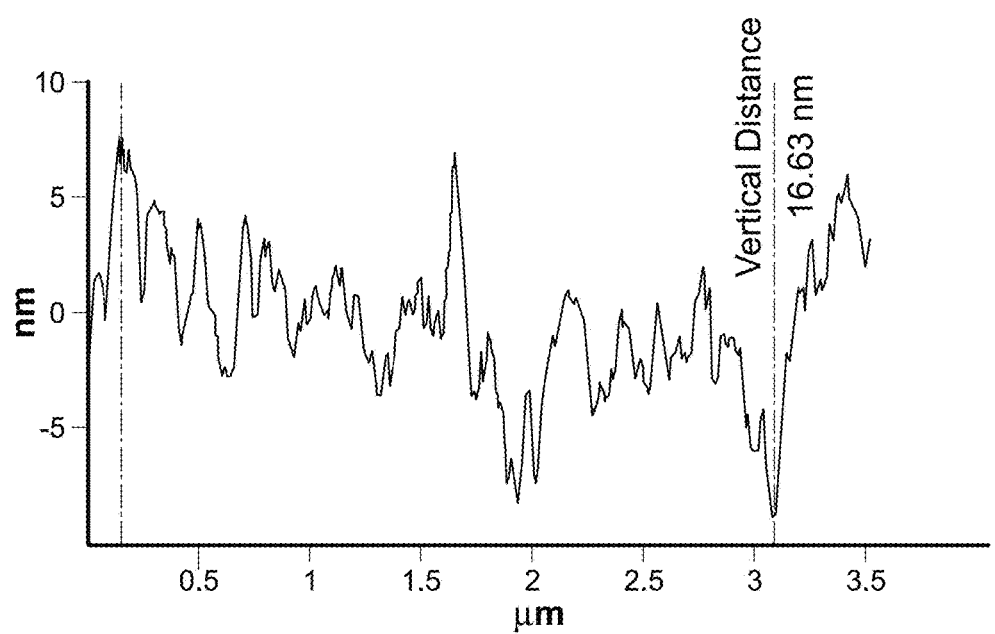
FIG. 4 is a graph illustrating the surface roughness of a hydrogel array as determined by atomic force microscopy.
Figure 6:
FIG. 6 is a side-on image showing individual hydrogel spots having different heights.

The method can further include placing a spacer between the patterned substrate and the surface-modified substrate. The spacer placed onto the patterned substrate while performing the method functions to define the height (or thickness) of the hydrogel forming the hydrogel array. A spacer may be particularly desirable when preparing higher (i.e., thicker) hydrogel arrays. Thus, the hydrogel array can have any desirable height (see e.g., FIG. 6). Suitable heights of the hydrogel array can be from about 20 micrometers (μm) to about 1 millimeter, however, hydrogel arrays can be made much higher than 1 millimeter if desired. The spacer also functions to prevent direct contact between the surface of the patterned substrate and the surface-modified substrate during formation of the hydrogel. The spacer used in the method can be any suitable material known to those skilled in the art. A particularly suitable spacer can be, for example, polydimethylsiloxane (PDMS). The height the hydrogel array can be determined, for example, using a microscope to focus from the top of the hydrogel down to the substrate, using a microscope to focus from the substrate up to the top of the hydrogel, and by measuring the surface roughness of a hydrogel array as determined by atomic force microscopy (see e.g., FIG. 4).

The preparation method further includes contacting a hydrogel precursor solution with the patterned substrate. In particular, the hydrogel precursor solution is contacted with the hydrophilic regions of the patterned substrate. The hydrophobic regions of the patterned substrate serve as a barrier between neighboring hydrophilic regions and also allow for the isolation of each hydrophilic region. The hydrogel precursor solution can be, for example, a combination of a polymer and a multifunctional polymer cross-linker.

When used as a hydrogel coating composition, preparation methods generally include contacting a hydrogel precursor solution with a substrate to be coated (e.g., surface of a cell culture plate).

Suitable polymers for use in the hydrogel precursor solution are known by those skilled in the art and can include, for example, poly(ethylene glycol), hyaluronic acid, gelatin, collagen, MATRIGEL®, dithiol polymers (e.g., acrylamide), click-based composite hydrogels (as discussed in Polizzotti et al. Biomacromolecules 2008, 9:1084-1087, which is hereby incorporated by reference to the extent its disclosure is consistent with the present disclosure), poly(ethylene glycol)-diacrylate, poly(ethylene glycol)-vinyl sulfone, and the like. Particularly suitable polymers can be, for example, poly(ethylene glycol). Particularly suitable polymers can be, for example, functionalized polymers. Functionalization of the polymer can be confirmed with $^1H$ nuclear magnetic resonance spectroscopy, mass spectroscopy, Elman's reagent, UV-Vis spectroscopy, infrared spectroscopy, and other methods known to those skilled in the art, for example.

A particularly suitable functionalized polymer can be, for example, eight-arm poly(ethylene glycol) with terminal hydroxyl (—OH) groups (commercially available from Jen-Kem Technology USA, Allen, Tex.) that is functionalized with norbornene. Eight-arm poly(ethylene glycol) can be functionalized with norbornene as described in Fairbanks et al. (Adv. Mater. 2009, 21:5005-5010).

Other particularly suitable polymers are poly(ethylene glycols) that may be functionalized using click chemistry. "Click" chemistry is an extremely versatile method for chemically attaching biomolecules, which is used to describe the [3+2] cycloaddition between alkyne and azide functional groups. Azides and alkynes are largely inert towards biological molecules and aqueous environments, which allows the use of the Huisgen 1,3-dipolar cycloaddition to yield stable triazoles that are very difficult to oxidize or reduce. Both the copper(I)-catalyzed and copper-free strained-alkyne variant reactions are mild and very efficient. These reactions can also be performed in small volumes of aqueous solutions, are insensitive to oxygen and water, and robust to functional groups on peptides. Click chemistry allows for selectivity in conjugation reactions in biological samples such as, for example, oligonucleotides and proteins. Particularly suitable reagents for click chemistry are commercially available from Laysan Bio Inc. (Arab, Ala.).

Generally, the hydrogel precursor solutions include concentrations of polymer of up to, and including, 200 mg/mL, including from about 36 mg/mL to about 160 mg/mL, and including from about 36 mg/mL to about 70 mg/mL.

Suitable multifunctional polymer crosslinkers for use in the hydrogel precursor solution are known by those skilled in the art. In particular, the multifunctional crosslinker can be, for example, a bifunctional polymer crosslinker and a multifunctional polymer crosslinker (n>=2) and terminated with a functional group that can form a covalent bond with the polymer of the hydrogel precursor solution. Particularly suitable bi-functional polymer crosslinkers and multifunctional polymer crosslinkers can be, for example, polyethylene glycol dithiol (PEG-DT), protease-degradable crosslinkers and multi-arm poly(ethylene glycol) terminated with thiol (e.g., 4-arm PEG terminated with thiol). Suitable protease-degradable crosslinkers can be, for example, matrix metalloproteinase (MMP)-degradable crosslinkers as described in Nagase and Fields (Biopolymers 1996, 40:399-416, which is hereby incorporated by reference to the extent it is consistent with the present disclosure). More particularly, suitable MMP-degradable crosslinking peptides for use in the hydrogel precursor solution include KCGGPQGIWGQGCK (SEQ ID NO:27) and KCGGPQGIAGQGCK (SEQ ID NO:28).

The hydrogel precursor solution can further include an initiator. As known by those skilled in the art hydrogel polymerization can occur in the absence of an initiator. An initiator can, however, induce polymerization and/or decrease the polymerization rate. Suitable initiators are known to those skilled in the art and can be, for example, chemical initiators and photoinitiators. Particularly suitable photoinitiators can be, for example, IRGACURE 2959 photoinitiator (commercially available from Ciba/BASF, Ludwigshafen, Germany) and Eosin Y. Polymerization to form the hydrogel can also be performed by temperature change.

In another aspect, the hydrogel precursor solution can include a cell adhesion peptide. As used herein, a "cell adhesion peptide" refers to an amino acid sequence obtained from an adhesion protein to which cells bind via a receptor-ligand interaction. Varying the cell adhesion peptide and concentrations thereof in the solution allow for the ability to control the stability of the cellular attachment to the resulting hydrogel composition. Suitable cell adhesion peptides include, for example, RGD, RGDS (SEQ ID NO:1), CRGDS (SEQ ID NO:2), CRGDSP (SEQ ID NO:3), PHSRN (SEQ ID NO:4), GWGGRGDSP (SEQ ID NO:5), SIDQVEPYSSTAQ (SEQ ID NO:6), GRNIAEIIKDI (SEQ ID NO:7), DITYVRLKF (SEQ ID NO:8), DITVTLNRL (SEQ ID NO:9), GRYVVLPR (SEQ ID NO:10), GNRWH-SIYITRFG (SEQ ID NO:11), GASIKVAVSADR (SEQ ID NO:12), GTTVKYIFR (SEQ ID NO:13), GSIKIRGTYS (SEQ ID NO:14), GSINNNR (SEQ ID NO:15), SDP-GYIGSR (SEQ ID NO:16), YIGSR (SEQ ID NO:17), GTPGPQGIAGQGVV (SEQ ID NO:18), GTPGPQ-GIAGQRVV (SEQ ID NO:19), MNYYSNS (SEQ ID NO:20), KKQRFRHRNRKG (SEQ ID NO:21), CRGDGGGGGGGGGGGGGPHSRN (SEQ ID NO:29), CPHSRNSGSGSGSGSGRGD (SEQ ID NO:30), Acetylated-GCYGRGDSPG (SEQ ID NO:31), CRDGS (SEQ ID NO:32), cyclic RGD{Fd}C (SEQ ID NO:33), RKRLQVQLSIRT (SEQ ID NO:37), IKVAV (SEQ ID NO:38), YIGSR (SEQ ID NO:39), KRTGQYKL (SEQ ID NO:40), TYRSRKY (SEQ ID NO:41), KRTGQYKLGSK-TGPGQK (SEQ ID NO:42), QAKHKQRKRLKSSC (SEQ ID NO:43), SPKHHSQRARKKKNKNC (SEQ ID NO:44), XBBXBX, wherein B=basic residue and X=hydropathic residue (SEQ ID NO:45), XBBBXXBX, wherein B=basic residue and X=hydropathic residue (SEQ ID NO:46), and RGDSP (SEQ ID NO:47).

The concentration of cell adhesion peptide in the hydrogel precursor solution will depend on the specific cell adhesion peptide being used as well as the other components in the hydrogel precursor solution. Typically, however, the hydrogel precursor solution includes from about 0.125 mM to about 4 mM cell adhesion peptide, including from about 0.25 mM to about 2 mM cell adhesion peptide. In one suitable embodiment, the cell adhesion peptide is CRGDS (SEQ ID NO:2), and the hydrogel precursor solution includes from about 0.25 mM to about 4 mM CRGDS (SEQ ID NO:2). In another suitable embodiment, the cell adhesion peptide is a cyclic RGD, and the hydrogel precursor solution includes from about 0.125 mM to about 2 mM cyclic RGD, particularly cyclic RGD{Fd}C (SEQ ID NO:33).

In another aspect, the hydrogel precursor solution can include a soluble factor binder. In one aspect, a peptide for binding a soluble factor contained in a cell culture medium is included in the hydrogel precursor solution. The density (concentration) of the soluble factor binder in a hydrogel composition can be controlled by altering the concentration of the soluble factor binder in the hydrogel precursor solution. Examples of particularly suitable soluble factor binders are provided in Table 1, below.

TABLE 1

Soluble factor binder peptide sequences for hydrogel compositions.

| Name/Source | Sequence | SEQ ID NO: |
| --- | --- | --- |
| Vascular Endothelial Growth Factor-Receptor Binding Peptide | GGGKLTWQELYQLKYKGI | 22 |
| Vascular endothelial growth factor receptor binding peptide (VR-BP) | KLTWQELYQLKYKGI | 23 |
| Bone morphogenetic protein-2 (BMP-2) receptor binding peptide | KIPKASSVPTEL | 24 |
| Bone morphogenic protein receptor-binding peptide | KIPKASSVPTELSAISTLYL | 25 |

TABLE 1-continued

Soluble factor binder peptide sequences for hydrogel compositions.

| Name/Source | Sequence | SEQ ID NO: |
|---|---|---|
| Heparin proteoglycan-binding peptide (HPG-BP) | KRTGQYKL | 26 |
| MMP-degradable peptide crosslinker | KCGGPQGIWGQGCK | 27 |
| MMP-degradable peptide crosslinker 2 | KCGGPQGIAGQGCK | 28 |
| VEGF binding peptide | CE{Fd}{Ad}{Yd}{Ld}IDENWEYPASK | 35 |
| Scrambled VEGF binding peptide | CD{Ad}PYN{Fd}EFAWE{Yd}VIS{Ld}K | 36 |

The concentration of soluble factor binder in the hydrogel precursor solution will depend on the specific soluble factor binder being used as well as the other components in the hydrogel precursor solution.

In another aspect, the hydrogel precursor solution can further include a cell. Suitable cells are known to those skilled in the art and can include, for example, an embryonic stem cell, an embryonic stem cell-derived neuron, an embryonic stem cell-derived neural progenitor cell, an embryonic stem cell-derived astrocyte, an embryonic stem cell-derived microglial cell, an embryonic stem cell-derived endothelial cell, an embryonic stem cell-derived retinal pigment epithelial cell, an induced pluripotent stem cell, an induced pluripotent stem cell-derived neural progenitor cell, an induced pluripotent stem cell-derived astrocyte, an induced pluripotent stem cell-derived microglial cell, an induced pluripotent stem cell-derived endothelial cell, a mesenchymal stem cell, an umbilical vein endothelial cell, an NIH 3T3 fibroblast, a dermal fibroblast, a fibrosarcoma cell, a valvular interstitial cell, a cardiomyocyte, an induced pluripotent stem cell-derived cardiomyocyte, an endothelial progenitor cell, a circulating angiogenic cell, a neuron, a pericyte, a cancer cell, a hepatocyte, a pancreatic beta cell, a pancreatic islet cell and combinations thereof.

In another aspect, the hydrogel precursor solution can further include a microsphere carrier (i.e., microcarrier). Microsphere carriers can contain molecules such as, for example, cells, biomolecules, dyes and other molecules known to those skilled in the art. Microspheres can be degradable microspheres that dissolve or degrade to release the contents of the microsphere.

Once prepared, the hydrogel precursor solution is contacted with a substrate (e.g., a patterned surface-modified substrate, surface of a cell culture plate, etc.).

When used on a patterned surface-modified substrate, the surface-modified substrate can be, for example, mica, glass, silicon, diamond and metal oxide surfaces. The surface-modified substrate can be prepared, for example, by functionalizing a surface such as a glass coverslip having a silane monolayer. A particularly suitable surface-modified substrate can be, for example, a glass slide. A particularly suitable method for functionalizing the substrate can be, for example, silanization. The substrate can be surface-modified by activating both sides of the surface in oxygen plasma treatment. Oxygen plasma treatment can increase the number of activated hydroxyl groups on the surface of the substrate. As known by those skilled in the art, a silane monolayer can be prepared with an alkoxysilane that is dissolved in an anhydrous organic solvent such as, for example, toluene. Other suitable alkoxysilanes can be for example, aminosilanes, glycidoxysilanes and mercaptosilanes. Particularly suitable aminosilanes can be, for example, (3-aminopropyl)-triethoxysilane, (3-aminopropyl)-diethoxy-methylsilane, (3-aminopropyl)-dimethylethoxysilane and (3-aminopropyl)-trimethoxysilane. Particularly suitable glycidoxysilanes can be, for example, (3-glycidoxypropyl)-dimethyl-ethoxysilane. Particularly suitable mercaptosilanes can be, for example, (3-mercaptopropyl)-trimethoxysilane and (3-mercaptopropyl)-methyldimethoxysilane. Other suitable silanes are commercially available (Sigma Aldrich, St. Louis, Mo.). Preparation of a surface-modified silane substrate can be performed using any silane having a terminal functional group that can participate in click chemistry as described herein. For example, mercaptosilane contains a terminal thiol that can react with the norbornene of the PEG-norbornene. Other suitable functional surface-modified silane substrates can be, for example, acrylates and methacrylates. Following surface-modification of the substrate, non-adhesive self-assembled monolayers are formed on the surface-modified substrate.

After contacting the substrate with the hydrogel precursor solution, the method includes polymerizing the hydrogel precursor solution such that polymerized hydrogel attaches (i.e., is coupled) to the substrate.

In one embodiment, the method can be used to form an array having "spots" or "islands" of hydrogel (referred to herein as "hydrogel spots") that are surrounded by a background that is substantially free, and even completely free, of hydrogel ("hydrogel-free"). In this embodiment, the hydrogel-free background corresponds to the hydrophobic regions of the patterned substrate and the hydrogel spots correspond to the hydrophilic regions of the patterned substrate. Referring to FIG. 1, the circles would represent the hydrogel spots that would be surrounded by a hydrogel-free region in this embodiment.

In another embodiment, the method can be used to form an array having hydrogel-free pools surrounded by a background of hydrogel (referred to herein as "a hydrogel background"). Referring to FIG. 1, the circles would represent the hydrogel-free pools that would be surrounded by the hydrogel-free background in this embodiment.

In another aspect, the present disclosure is directed to a hydrogel compositions including hydrogel spots having variable modulus, variable shear modulus, variable ligand identity, variable ligand density and combinations thereof. Hydrogel compositions having variable modulus, variable shear modulus, variable ligand identity, variable ligand density and combinations thereof can be prepared according to the methods described herein above.

Suitable ligands are known to those skilled in the art and can be, for example, any biomolecule containing a cysteine and/or functionalized with a thiol. Thiol-functionalizing of ligands can be performed using commercially available kits (e.g., Traut's Reagent (2-iminothiolane.HCl), Thermo Fischer Scientific, Rockford, Ill.). Suitable ligands can be, for example, proteins, peptides, nucleic acids, polysaccharides, lipids, biomimetic materials and other molecules, and combinations thereof. Particularly suitable proteins can be, for example, adhesion proteins. Particularly suitable adhesion proteins can be, for example, fibronectin, cadherin and combinations thereof. Particularly suitable peptides can be, for example, cell adhesion peptides and/or soluble factor binders, as described herein above.

Suitably, the hydrogel compositions of the present disclosure include combinations of cell adhesion peptides and soluble factor binders that are suspected of binding or interacting with a cell to affect cell attachment, spreading, migration, maturation, proliferation, differentiation, and formation of cellular structures (e.g., tubules).

Hydrogel compositions may further include variable moduli. Hydrogel compositions can have a range of stiffness (expressed herein as substrate elastic moduli). For example, hydrogels with different moduli can be prepared by changing the concentration of the polymer and/or changing the stoichiometric ratio of the multifunctional polymer (e.g., the bifunctional polymer thiol-polyethylene glycol-thiol (SH-PEG-SH)) to polymer ratio in the hydrogel precursor solution (see e.g., FIG. 8). Suitable ratios can be from about 1:1 to about 4:1 (molar ratio).

In another aspect, the patterned hydrogel array can be further assembled with a microarray add-on whereby the patterned hydrogel array is prepared with dimensions to accommodate add-ons of any size. Suitable microarray add-ons are commercially available (Grace Bio Labs, Bend, Oreg.). A microarray add-on can allow for the isolation of each individual hydrogel spot and hydrogel-free pool of the hydrogel array such that soluble factor presentation can be controlled. The microarray add-on can include the same number of openings as the number of individual hydrogel spots and hydrogel-free pools of the hydrogel array such that each hydrogel spot and hydrogel-free pool can be independently interrogated with soluble factor presentation. Alternatively, the microarray add-on can have larger openings that can accommodate more than one individual hydrogel spot and more than one individual hydrogel-free pool. For example, a microarray add-on can have openings large enough to accommodate a single hydrogel spot or a single hydrogel-free pool.

Methods of Using the Hydrogel Compositions

In another aspect, the present disclosure is directed to methods of using the hydrogel compositions to promote cellular expansion, maturation and cellular differentiation. Generally, the methods include preparing the hydrogel compositions; contacting a cell with the hydrogel compositions; and culturing the cells. The hydrogel compositions are prepared as described above and typically include a polymer (e.g., a polyethylene glycol functionalized with norbornene), a multifunctional polymer crosslinker (e.g., MMP-degradable crosslinking peptide, non-degradable PEG-dithiol crosslinker), and a cell adhesion peptide as described more fully above.

The method further includes contacting a cell with the hydrogel composition. As used herein, "contacting a cell" refers to seeding the cells with the purpose of culturing the cells. As known by those skilled in the art a cell suspension is typically transferred to a substrate and cells are given sufficient time to adhere to the substrate.

In another embodiment, cells can be incorporated into the hydrogel of the hydrogel compositions using a hydrogel precursor solution that includes the polymer, the crosslinker, the cell adhesion peptide, and the cell.

The cells are then cultured for a desired time such as, for example, about one hour to about 30 days. After the desired time, cells can be analyzed by microscopy such as, for example, immunofluorescence microscopy, phase contrast microscopy, light microscopy, electron microscopy and combinations thereof. Cells can be analyzed for cell attachment, cell spreading, cell morphology, cell proliferation, cell migration, cell expansion, cell differentiation, protein expression, cell-to-cell contact formation, sprouting, tubulogenesis, formation of structures, and combinations thereof.

Suitable cells can be any cell known by those skilled in the art. Particularly suitable cells can include, for example, an embryonic stem cell, an embryonic stem cell-derived neuron, an embryonic stem cell-derived neural progenitor cell, an embryonic stem cell-derived astrocyte, an embryonic stem cell-derived microglial cell, an embryonic stem cell-derived endothelial cell, an embryonic stem cell-derived retinal pigment epithelial cell, an induced pluripotent stem cell, an induced pluripotent stem cell-derived neural progenitor cell, an induced pluripotent stem cell-derived astrocyte, an induced pluripotent stem cell-derived microglial cell, an induced pluripotent stem cell-derived endothelial cell, an induced pluripotent stem cell-derived retinal pigment epithelial cell, a mesenchymal stem cell, an umbilical vein endothelial cell, an NIH 3T3 fibroblast, a dermal fibroblast, a fibrosarcoma cell, a valvular interstitial cell, a cardiomyocyte, an induced pluripotent stem cell-derived cardiomyocyte, an endothelial progenitor cell, a circulating angiogenic cell, a neuron, a pericyte, a cancer cell, a hepatocyte, a pancreatic beta cell, a pancreatic islet cell and combinations thereof.

In one particular aspect, the cell is a circulating angiogenic cell CAC). CACs are pro-angiogenic cell population that fulfills many roles in vascular biology including the formation of new blood vessels during healing. While CACs are a promising tool for treatment of multiple cardiovascular disorders including peripheral ischemia and restoration of damaged or dysfunctional endothelium; harvesting of CACs is challenging due to their scarcity in the blood stream, so only small numbers of CACs can be isolated at any one time. By culturing the CACs in the hydrogel compositions of the present disclosure, prepared using hydrogel precursor solutions that encourage proliferation of recruited CACs, the above problem of low initial numbers of recruited CACs and limited CAC expansion is addressed.

In one particular aspect, when used with CACs, the hydrogel compositions include 8-arm, 20 kDa poly(ethylene glycol) (PEG) functionalized with norbornene, a MMP degradable crosslinking peptide, and a cell adhesion peptide. Particularly suitable cell adhesion peptides include immobilized RGD-containing peptides, including CRGDS (SEQ ID NO:2), Acetylated-GCYGRGDSPG (SEQ ID NO:31); cyclic {RGD(Fd)C} (SEQ ID NO:33); CRGD-(G)13-PHSRN (SEQ ID NO:29); and CPHSRN-(SG)5-RGD (SEQ ID NO:30). Suitably, the hydrogel compositions include at least about 1 mM cell adhesion peptide, including from about 1 mM to about 4 mM cell adhesion peptide. Further, the hydrogel compositions may include from about 20 mg/mL to about 100 mg/mL PEG concentration.

In some aspects, the hydrogel compositions are prepared to include cros slinking to an extent of at least 35%, including at least 45%, and including from about 35% to about 75%, and including from about 45% to about 50%.

Suitably, the hydrogel compositions for use with CACs including a shear modulus in the range of from about 1.8 kPa to about 12 kPa, including from about 2 kPa to about 12 kPa.

In another aspect, the cell is a human mesenchymal stem cell (hMSC). It has been found that PEG-hydrogel compositions support hMSC adhesion and expansion. Further, these hydrogel compositions offer combinatorial control over substrate stiffness, cell adhesion, and growth factor regulation.

In one particular aspect, when used with hMSC, the hydrogel compositions include 8-arm, 20 kDa poly(ethylene glycol) (PEG) functionalized with norbornene, a MMP degradable crosslinking peptide, and a cell adhesion peptide. Particularly suitable cell adhesion peptides include immobilized RGD-containing peptides, including CRGDS (SEQ ID NO:2), Acetylated-GCYGRGDSPG (SEQ ID NO:31); cyclic {RGD(Fd)C} (SEQ ID NO:33); CRGD-(G)13-PH-SRN (SEQ ID NO:29); and CPHSRN-(SG)5-RGD (SEQ ID NO:30). Suitably, the hydrogel compositions include at least about 0.25 mM cell adhesion peptide, including from about 0.25 mM to about 4 mM cell adhesion peptide, and including from about 1 mM to about 4 mM cell adhesion peptide. Further, the hydrogel compositions may include from about 40 mg/mL to about 160 mg/mL PEG concentration.

Further, the hydrogel compositions for use with hMSCs possess a shear modulus of at least 1.8 kPa, including a shear modulus of from about 1.8 kPa to about 33 kPa, and including from about 1.8 kPa to about 10.9 kPa.

In another aspect, the cell includes a human pluripotent stem cell (hPSC) such as, for example, human embryonic stem cells (hESC) and human induced pluripotent stem cells. Similar to hMSC, it has been found that PEG-hydrogel compositions, and particularly, hydrogel compositions including (PEG) functionalized with norbornene, a MMP degradable crosslinking peptide, and a cell adhesion peptide (e.g., cyclic {RGD(Fd)C} (SEQ ID NO:33), offer substrate stiffness control, cell adhesion control, and growth factor regulation, thereby supporting hPSC adhesion and expansion. Suitably, the hydrogel compositions include at least about 0.25 mM cell adhesion peptide, including from about 0.25 mM to about 4 mM cell adhesion peptide, and including from about 2 mM to about 4 mM cell adhesion peptide.

Further, the hydrogel compositions for use with hPSCs possess a shear modulus of at least 3 kPa, including a shear modulus of from about 3 kPa to about 16 kPa, and including from about 3 kPa to about 10 kPa.

In a further aspect, the hydrogel compositions further include immobilized low molecular weight heparin. Suitably, when present, the hydrogel composition includes low molecular weight heparin in amounts ranging from about 0.1 mM to about 2 mM.

The method may further include contacting the cell with a soluble molecule by including the soluble molecule in the culture medium in which the cells are cultured. Particularly suitable soluble molecules can be growth factors and proteoglycans. Suitable growth factors can be, for example, proteins from the transforming growth factor beta superfamily, fibroblast growth factor family of growth factors, platelet derived growth factor family of growth factors and combinations thereof. Particularly suitable growth factors can be, for example, vascular endothelial growth factor, bone morphogenetic proteins, fibroblast growth factor, insulin-like growth factor and combinations thereof. Suitable proteoglycans and be, for example, proteoglycans with heparin, heparin sulfate, and/or chondroitin glycosaminoglycan side chains.

The disclosure will be more fully understood upon consideration of the following non-limiting Examples.

EXAMPLES

Materials and Methods
PEG-Norbornene Synthesis

Eight-arm poly(ethylene glycol) (PEG) with terminal hydroxyl groups (—OH) and a molecular weight of 20 kDa was purchased from JenKem Technology USA (Allen, Tex.). Anhydrous pyridine, 4-dimethylamino)pyridine (DMAP), 5-norbornene-2-carboxylic acid, diethyl ether, and deuterated chloroform ($CDCl_3$, 99.8%) with 0.03% v/v tetramethylsilane (TMS) were purchased from Sigma Aldrich (St. Louis, Mo.). N,N'-Dicyclohexylcarbodiimide (DCC) and anhydrous dichloromethane (DCM) were purchased from ACROS Organics (Geel, Belgium). SNAKESKIN dialysis tubing having a 3.5K molecular weight cut-off was purchased from Thermo Fisher Scientific (Waltham, Mass.).

Eight-arm PEG-OH was functionalized with norbornene to utilize the thiol-ene chemistry for photopolymerization and immobilization of bioactive ligands (as described in Fairbanks et al. Adv. Mater. 2009, 21:5005-5010; Impellitteri et al. Biomaterials 2012, 33:3475-84; Belair and Murphy Acta Biomater. 2013; and Gould et al. Acta Biomater 2012, 8:3201-3209). The PEG-norbornene (PEG-NB) product of the functionalization reaction was filtered through a medium fritted Buchner funnel to remove salts formed during the reaction. The filtrate was then precipitated in 900 mL cold diethyl ether and 100 mL hexane. The solids were collected on qualitative grade filter paper and air dried overnight. The PEG-NB product was purified by dialysis against 4 L of $dH_2O$ at 4° C. for 72 hours (with water change every 8 hours) using rehydrated SNAKESKIN dialysis tubing to remove residual norbornene acid and subsequently freeze dried.

Norbornene functionalization of >90% was confirmed with 1H nuclear magnetic resonance spectroscopy. Samples were prepared at 6 mg/mL in $CDCl_3$ with TMS internal standard. Free induction decay (FID) spectra were obtained using spectroscopy services provided by the National Magnetic Resonance Facility at Madison on a Bruker Instruments Avance III 500i spectrometer at 400 MHz and 27° C.
Hydrogel Array Formation Hydrogel arrays used for these experiments were composed of hydrogel spots immobilized on silanized glass substrates. Hydrogel spots were formed using gold surfaces patterned to possess regions with differential wettability, whereby the pattern was defined by an elastomeric stencil. The method of preparing the hydrogel arrays is further described below.
Glass Silanization Glass coverslips and hydrochloric acid (HCl) solution were purchased from Thermo Fisher Scientific (Waltham, Mass.). Toluene, methanol, ethanol, 3-mercaptopropyl trimethoxysilane (3-MPTS), and dithiothreitol (DTT) were purchased from Sigma Aldrich (St. Louis, Mo.). A low pressure plasma system was purchased from Diener Electronic (Ebhausen, Germany).

Glass coverslips were silanized with 3-MPTS to create substrates presenting thiol groups capable of participating in thiol-ene reaction with PEG-NB and subsequently enable covalent immobilization of PEG-NB hydrogels (Seo et al. Colloids Surf B Biointerfaces 2012, 98:1-6). Liquid-phase silanization was performed as previously described (Seo et al. Colloids Surf B Biointerfaces 2012, 98:1-6; Halliwell et al. Anal Chem 2001, 73:2476-2483; and Cras et al. Biosens Bioelectron 1999, 14:683-688). Coverslips were sonicated for 45 minutes in 1:1 methanol to HCl to remove bulk contaminants Immediately prior to silanization, coverslips were activated by oxygen plasma treatment at 40 sccm and 50 W for 5 minutes on each side to increase the number of activated hydroxyl groups on the surface. Activated coverslips were placed in a coplin jar containing 2.5% v/v 3-MPTS in toluene for 4 hours. Excess silanes were removed from the surface of the coverslips by rinsing with toluene, 1:1 ethanol/toluene, and ethanol and dried with $N_2$ gas. Silanized coverslips were placed in an airtight chamber, purged with $N_2$ gas, and cured at 100° C. for 1 hour to crosslink the silanes coupled to the surface and reduce their susceptibility to hydrolysis. Silanized coverslips were stored in the $N_2$ gas purged chamber and protected from light until use. Prior to use, silanized glass coverslips were treated with 10 mM DTT in PBS for 30 minutes at 37° C. to reduce disulfides formed on the surface and to increase free thiols available at the surface (Vistas et al. Appl Surf Sci 2013, 286:314-318).

Fabrication of Elastomeric Stencils

Silicon wafers were purchased from WRS Materials (San Jose, Calif.). SU-8 100 photoresist was purchased from MicroChem (Newton, Mass.). Sylgard 184 silicone elastomer kit was purchased from Dow Corning Corporation (Midland, Mich.).

Polydimethylsiloxane (PDMS) elastomeric stencils were created using soft lithography as previously described (Jo et al. J Microelectromechanical Syst 2000, 9:76-81). The layout and geometries for the stencil were drawn using Adobe Illustrated, printed onto transparency films using a high resolution commercial laser printing service provided by ImageSetter (Madison, Wis.). The transparency film was used as a photo mask in combination with conventional photolithography techniques to create master molds with SU-8 negative-tone UV photoresist spin-coated on silicon wafers. To create the PDMS stencil, the curing agent and PDMS pre-polymer solution from the Sylgard elastomer kit were thoroughly mixed in a 1:10 weight ratio, spread onto the master mold, and cured at 80° C. for 6 hours. After curing, the PDMS stencils were peeled off from the master mold, briefly cleaned with ethanol, and dried with $N_2$ gas.

Hydrophobic/Hydrophilic Patterning

Gold-coated test slides (1,000 Å gold on 50 Å titanium metal thin films on 25 mm×75 mm×1 mm glass) were purchased from Evaporated Metal Films (Ithaca, N.Y.). Perfluorinated alkanethiol (HS—$(CH_2)_{11}$—O—$(CH_2)_2$—$(CF_2)_5$—$CF_3$) was purchased from ProChimia Surfaces (Sopot, Poland). Hydroxyl-terminated alkanethiol (HS—$C_{11}$—(O—$CH_2$—$CH_2)_3$—OH) was synthesized as previously described (Prime and Whitesides J. Am. Chem. Soc. 1993, 115:10714-10721).

Gold-coated slides were patterned with hydrophobic and hydrophilic self-assembled monolayers (SAMs) of alkanethiolates to form regions with differential wettability. Differential wettability patterning served two purposes simultaneously: 1) defined the geometries of the hydrogel spots and 2) confined the contents of each hydrogel spot in the array. Gold-coated slides were immersed in ethanol and sonicated for ~2 minutes, rinsed with ethanol, and dried with $N_2$ gas to remove contaminants and gold oxide layers. Gold-coated slides were immersed in a 1 mM perfluorinated alkanethiol in ethanol solution for >2 hours to allow for perfluorinated alkanethiolate SAMs (fluoraSAMs) formation. After fluoraSAMs formation, fluoraSAMs gold-coated slides were cleaned with ethanol and dried with $N_2$ gas. To define hydrophilic regions on the substrate, PDMS stencils were placed on the fluoraSAMs gold-coated slides to selectively protect areas of the slides from plasma etching. The spatial and geometric patterning of the exposed regions on the fluoraSAMs gold-coated slides were defined by the pattern of the PDMS stencil, which, in turn, defined the geometry and spatial patterning of the hydrogel spots that the arrays could comprise. Exposed regions of the fluoraSAMs gold-coated slides were etched by oxygen plasma treatment at 40 sccm and 50 W for 1 minute. The etched gold-coated slides were cleaned with ethanol and dried with $N_2$ gas and immersed in a 0.1 mM hydroxyl-terminated alkanethiol in ethanol solution for >2 hours so that hydrophilic alkanethiolate SAMs ($EG_3SAMs$) were formed in the selectively-etched regions of the gold-coated slides. The resulting gold-coated slides with differential wettability were cleaned with ethanol and dried with $N_2$ gas before hydrogel formation.

Figure 2A:
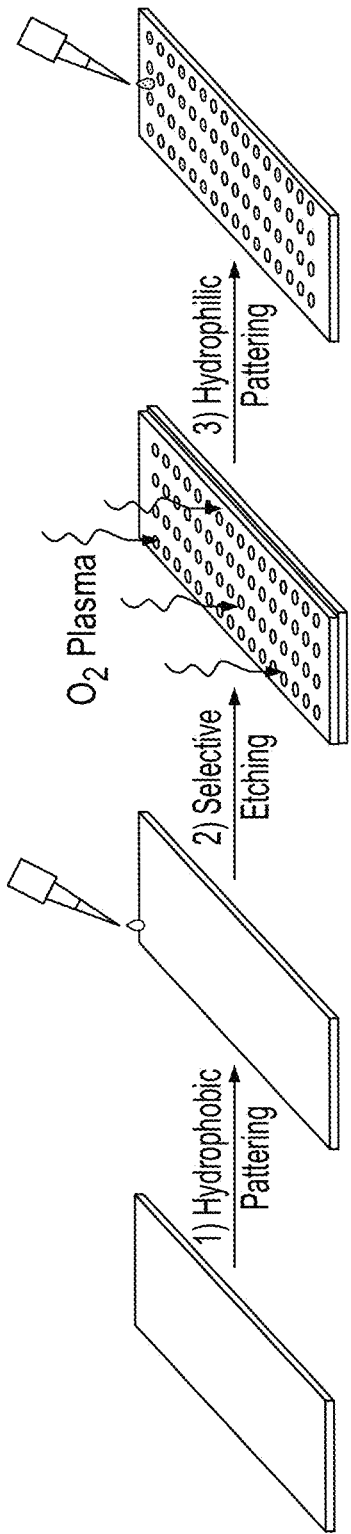
FIG. 2A is a schematic illustration of the steps for patterning a metal-coated substrate used in the method for preparing a hydrogel array of the present disclosure.
Figure 2B:
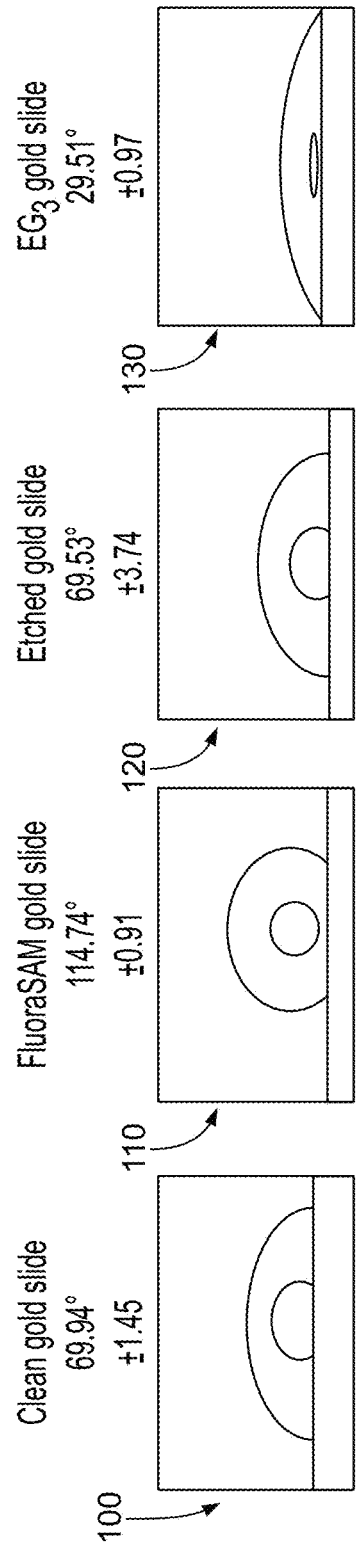
FIG. 2B are end view drawings of the metal-coated substrate during the steps for patterning a metal-coated substrate shown in FIG. 2A.

Hydrophobic and hydrophilic SAMs formation on the gold-coated slides were confirmed with contact angle measurements (see, FIG. 2B). Static contact angles were measured at room temperature using a contact angle goniometer (DataPhysics Contact Angle System OCA, San Jose, Calif.). A drop of distilled water (3 μL) was placed on the surface and the static contact angle was measured for 3 different samples at five different sites on each sample and averaged.

Hydrogel Spot Polymerization and Immobilization

PEG-NB was functionalized as described above. Bi-functional PEG dithiol (PEG-DT) crosslinker (3.4 kDa) was purchased from Laysan Bio (Arab, Ala.). IRGACURE 2959 photoinitiator was purchased from Ciba/BASF (Ludwigshafen, Germany). Cysteine-terminated peptides were purchased from GenScript USA (Piscataway, N.J.). Omnicure Series 1000 UV spot cure lamp (365 nm wavelength), light guide, and collimating adapter were purchased from Lumen Dynamics Group (Ontario, Canada). PDMS spacers with thickness dimensions corresponding to the desired hydrogel spot heights were fabricated using the same procedure as stated above.

Hydrogel precursor solutions were prepared by combining PEG-NB, PEG-DT, peptides, and photoinitiator and diluted to desired concentrations with phosphate buffered saline (PBS) immediately prior to hydrogel spots formation. To form each hydrogel array, a patterned gold-coated slide was rinsed with ethanol and dried with $N_2$ gas, PDMS spacers were placed onto hydrophobic regions of the slide, and hydrogel precursor solutions were spotted onto the hydrophilic regions. A DTT-treated silanized glass coverslip was used to sandwich the hydrogel precursor solutions between the coverslip and the slide. Hydrogel precursor solutions were polymerized by UV-initiated photo-cross-linking for 2 seconds at 90 mW/cm$^2$, with the light penetrating through the glass coverslip. The resulting polymerized hydrogel spots were covalently attached and immobilized onto the coverslip. Recall that the silanization procedure produced glass coverslips that were functionalized with thiol-terminated silanes that were capable of participating in the thiol-ene reaction used for hydrogel precursor solution polymerization, which effectively crosslinked the hydrogel network to the surface-bound silanes.

The gold-coated slide was separated from the coverslip, which enabled the glass-immobilized hydrogel spots to cleanly detach from the gold-coated slide. The resulting glass-immobilized hydrogel spots, collectively referred to as the "hydrogel array", was sterilized for 1 hour in 70% ethanol and washed with PBS to remove any remaining unreacted components.

The bioactivity of each hydrogel spot in the array was defined by both the identity and concentration of the peptides incorporated therein. Peptides used in this study were CRGDS (SEQ ID NO:2), CRGD-(G)$_{13}$-PHSRN (SEQ ID NO:29), CRGD-(SG)$_5$-PHSRN (SEQ ID NO:30), acetylated-CRGDSP (SEQ ID NO:31), cyclic (RGD{Fd}C) (SEQ ID NO:33), and a non-bioactive scrambled peptide CRDGS (SEQ ID NO:32). To modulate the bioactivity of each hydrogel spot, different peptides were added to the hydrogel precursor solutions and, following UV-initiated crosslinking, the resulting polymerized hydrogel networks each presented different immobilized peptides. For all arrays, a total of 4 mM of peptides were incorporated into the hydrogel network. To concurrently change the bioactivity of the hydrogel spots via control of peptide identity and concentration, the desired concentration of the chosen bioactive peptide (containing the "RGD" sequence) was determined and the CRDGS (SEQ ID NO:32) peptide was supplemented to maintain a total peptide concentration of 4 mM in the hydrogel precursor solution.

The modulus of each hydrogel spot in the hydrogel array was defined by the total concentration of PEG in the crosslinked hydrogel network. Increasingly, the concentration of PEG-NB in the hydrogel precursor solution resulted in a larger amount of PEG crosslinked into the polymerized network, which resulted in an increase in the compressive modulus (see, FIG. 8).

Example 1

In this Example, a hydrogel array immobilized on a glass substrate was prepared.

Figure 1B:
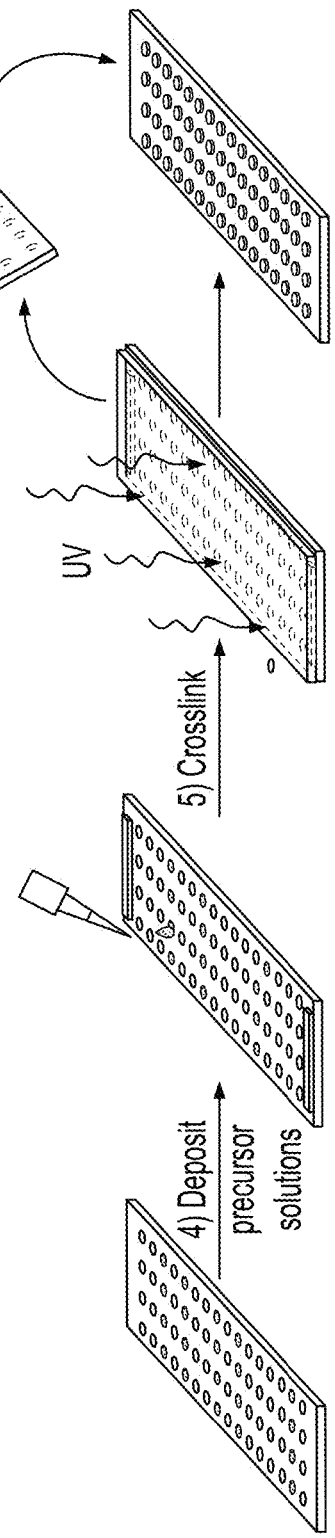

A gold substrate was modified with a patterned alkanethiolate self-assembled monolayer (SAMs) to provide isolated hydrophilic regions separated by a surrounding hydrophobic region (as illustrated in FIGS. 1A-1B). As illustrated in FIG. 2A (also shown in FIG. 1A), hydrophobic and hydrophilic SAMs formation on the gold-coated slides were confirmed with contact angle measurements. FIG. 2B provides end views during patterning of a gold substrate at the step before hydrophobic patterning 100; of the substrate having fluoraSAMs 110; of the substrate after etching 120; and of the substrate after hydrophilic patterning 130.

Figure 3:
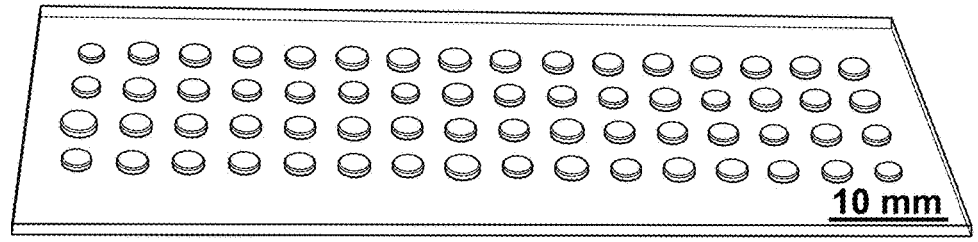
FIG. 3 is a photograph of a hydrogel array with 64 individual hydrogel spots prepared using the methods of the present disclosure.

Hydrogel precursor solutions containing all components required for polymerization reactions were deposited onto the hydrophilic SAMs regions of the patterned substrate (see, FIG. 1B). The hydrophilic regions served to both confine the contents of the solutions deposited onto each region and to define the geometries of the resulting polymerized hydrogel. Elastomeric spacers (with thickness dimensions equivalent to the desired hydrogel array height) were placed onto the hydrophobic areas of the patterned slide to define the height of the hydrogel array. A glass substrate, modified by silanization to possess SAMs with end-functional groups capable of participating in the polymerization reaction, was used to sandwich the hydrogel precursor solution. During the UV polymerization, the components of the hydrogel precursor solution formed a crosslinked network as well as formed covalent bonds with the end-function groups on the glass substrate. The polymerized hydrogels removed cleanly from the patterned gold substrate to produce a hydrogel array immobilized on the glass substrate (see, FIG. 3).

Example 2

In this Example, a hydrogel array was used to determine the effects of substrate properties on initial stem cell adhesion.

Figure 9:
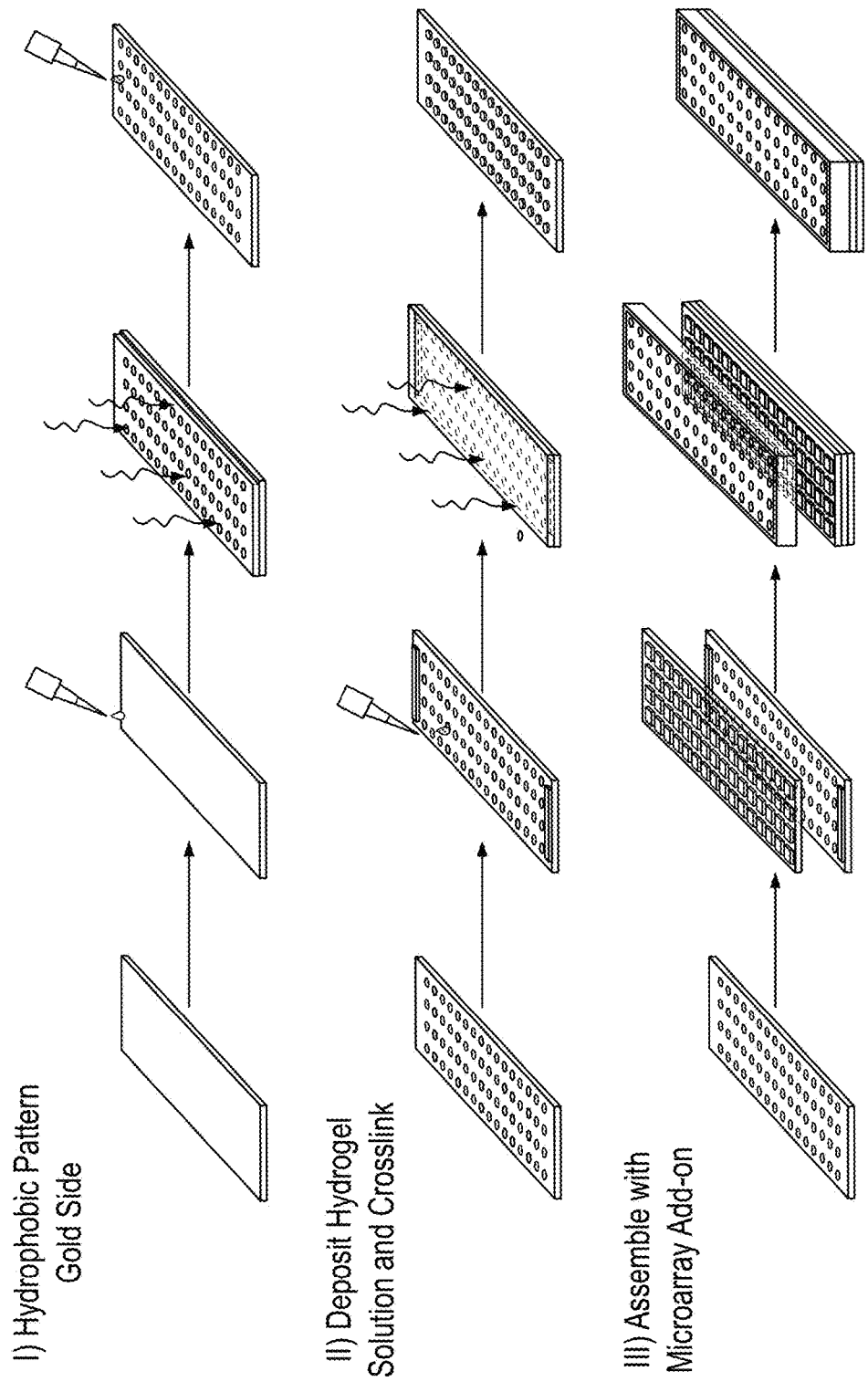
FIG. 9 is a schematic illustrating the steps for preparing a hydrogel array and further assembling the hydrogel array with a microwell add-on using the methods of the present disclosure.
Figure 10A:
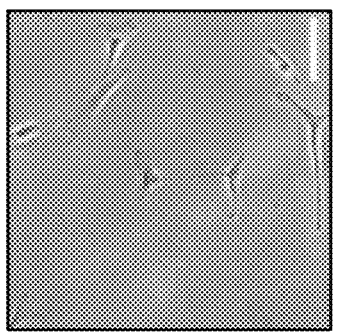
FIG. 10A-10C are photographs of hMSCs cultured on hydrogel arrays prepared using 4 wt. % (FIG. 10A), 6 wt. % (FIG. 10B) and 8 wt. % (FIG. 10C) polyethylene glycol and presenting linear RGD peptide, as discussed in Example 2. Scale bar=100 μm.
Figure 10B:
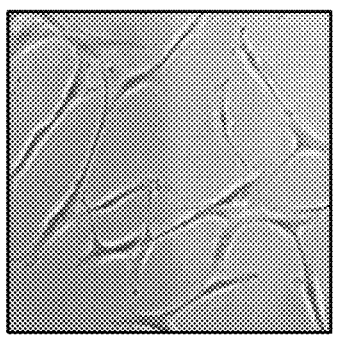
Figure 10C:
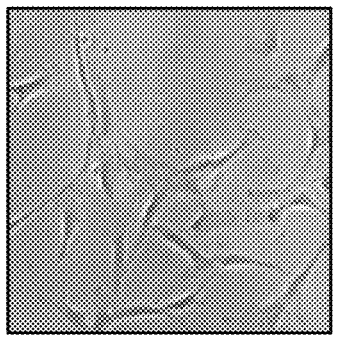

Poly(ethylene glycol) (PEG) hydrogel arrays were formed using patterned hydrophobic/hydrophilic self-assembled monolayers on gold substrates to both define the geometry and confine the contents of each hydrogel spot in the array as described above (see, FIGS. 1A-1B). UV-initiated thiol-ene crosslinking simultaneously polymerized the hydrogel and immobilized the hydrogel spots on the glass to result in the hydrogel array. As illustrated in FIG. 9, hydrogel arrays could be prepared with dimensions compatible with a 64-well microarray add-on (commercially available from Grace Bio-Labs, Bend, Oreg.).

Figure 7:
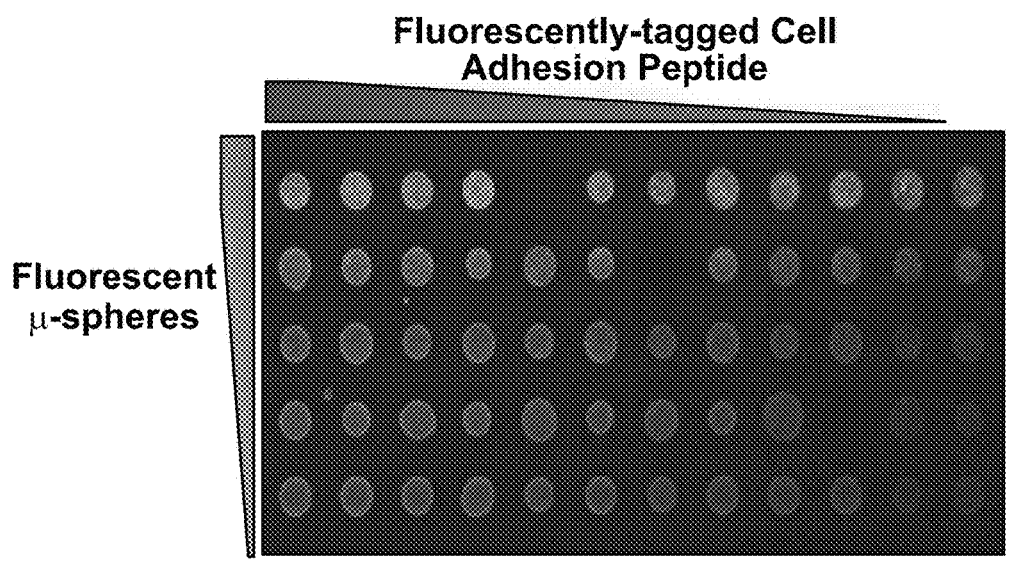
FIG. 7 is a hydrogel array showing differential patterning of individual hydrogel spots by increasing the density of a fluorescently-tagged peptide and increasing the density of encapsulated fluorescent microspheres, as discussed in Example 2.
Figure 8:
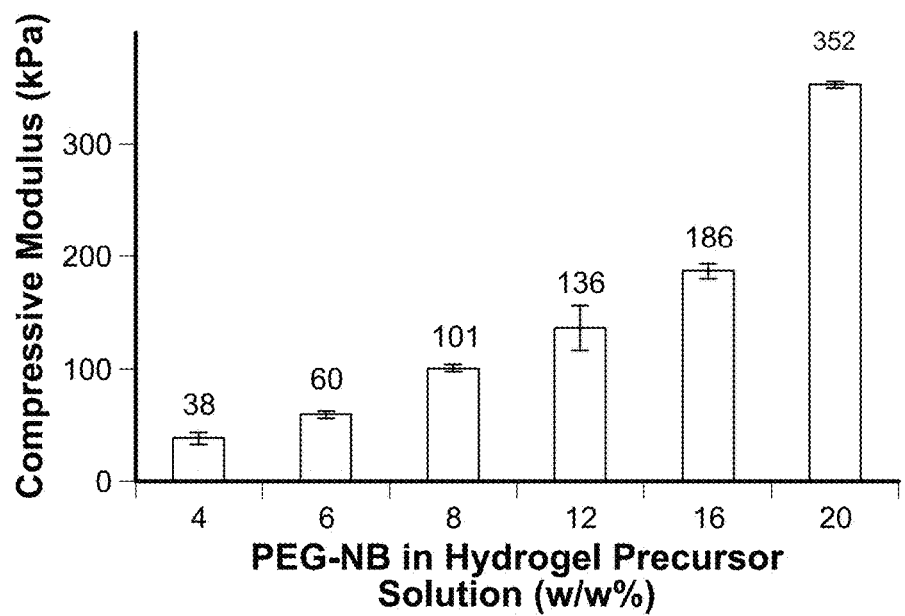
FIG. 8 is a graph illustrating control of the modulus of individual hydrogel spots of a hydrogel array by changing the total concentration of PEG-NB (w/w %) in the hydrogel precursor solution using the methods of the present disclosure.

Hydrogel solutions with fibronectin-derived peptides, fluorescent microspheres and a dithiol crosslinker were deposited onto the SAMs and sandwiched with a silanized glass slide. As shown in FIG. 7, individual hydrogel spots of the hydrogel array could be prepared to include varying amounts of fluorescently-tagged peptides as well as varying amounts of fluorescent microspheres. Hydrogel solutions with varying PEG or crosslinker concentration were also prepared prior to crosslinking to change the stiffness, peptide identity or peptide concentration (FIG. 8). The resultant arrays (see, FIG. 3) included 2.4 mm diameter, 150 um height posts. Human mesenchymal stem cells (hMSCs) were cultured on posts with varying PEG concentrations (4 wt %, 6 wt % and 8 wt %) to change stiffness and monitored for changes in initial cell adhesion and spreading. Human embryonic stem cells (hESCs) were cultured on posts with varying peptide identity (blank, RDGS, RGDS (SEQ ID NO:1), RGD-PHSRN (SEQ ID NO:34), RGDSP (SEQ ID NO:47), and cyclic RGD) and monitored for changes in initial cell adhesion and spreading.

Figure 11A:
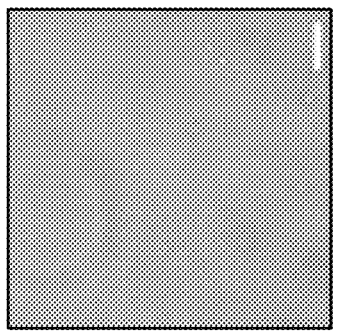
FIG. 11A-11C are photographs of hESCs cultured on hydrogel arrays prepared using 4 wt. % (FIG. 11A), 6 wt. % (FIG. 11B) and 8 wt. % (FIG. 11C) polyethylene glycol and presenting varying peptide identity, as discussed in Example 2. Scale bar=100 μm.
Figure 11B:
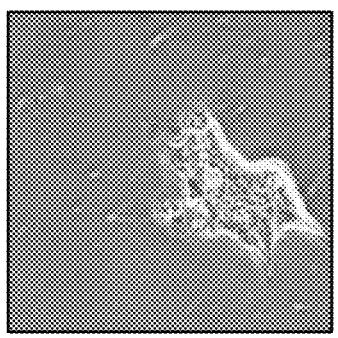
Figure 11C:
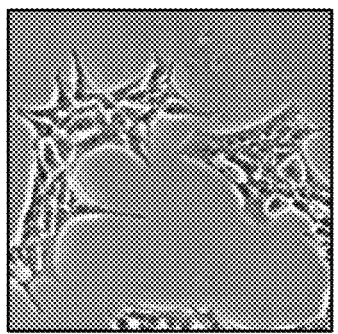

As shown in FIGS. 10A-10C, 2D culture of hMSCs demonstrated cell spreading dependence in response to changes in modulus consistent with published observations (see, Engler et al. Cell 126:677 (2006)). 2D culture of hESCs in chemically-defined, albumin-free media demonstrated that cell adhesion was highly specific to peptide-presenting spots. Both hESC cell adhesion and spreading were dependent on the binding affinity of integrin receptors to immobilized peptides (see, FIG. 11). Arrays allowed for changes in hydrogel spot shape, hydrogel spot height (by changing patterned hydrogel spot shapes or adding spacers), hydrogel spot stiffness and hydrogel spot peptide concentrations, and was adaptable for both 2D and 3D cell culture.

These results demonstrate that the method for preparing hydrogel arrays as described herein provides the capability to control stiffness, immobilized ligand identity and ligand concentration (density), and soluble growth factor presentation. The hydrogel arrays of the present disclosure can support cell adhesion and survival and allow for screening complex cell-environment interactions.

Example 3

In this Example, the hydrogel compositions of the present disclosure were prepared, human mesenchymal stem cells (hMSCs) were cultured thereon, and cell properties were analyzed.

Hydrogel arrays containing hydrogel spots with stiffness values ranging from 1.8 to 10.9 kPa and varying immobilized CRGDS (SEQ ID NO:2) peptide concentrations from 0 to 4 mM were prepared as described herein. Note that total peptide concentration was maintained at 4 mM by supplementing the hydrogel precursor solution with a "scrambled", non-bioactive CRDGS peptide (SEQ ID NO:32). The stiffness range selected for this screen was chosen to reflect the reported stiffness values of various soft tissues, including fat and muscle tissue. Following hydrogel array formation, hMSCs were seeded onto the hydrogel spots and cultured for up to 8 days.

Independent of hydrogel spot stiffness, hMSC initial cell attachment, spreading, and proliferation were linearly correlated with immobilized CRGDS (SEQ ID NO:2) concentration. After 1 day of culture, minimal hMSCs were attached to hydrogel spots that did not contain CRGDS (SEQ ID NO:2) (4 mM "scrambled" CRDGS (SEQ ID NO:32)), indicating that initial cell adhesion was mediated by the bioactivity of the immobilized peptide. Increased CRGDS (SEQ ID NO:2) concentration resulted in increased hMSC cell attachment, spreading, and proliferation with maximal values on hydrogel spots presenting 4 mM CRGDS (SEQ ID NO:2).

Figure 12:
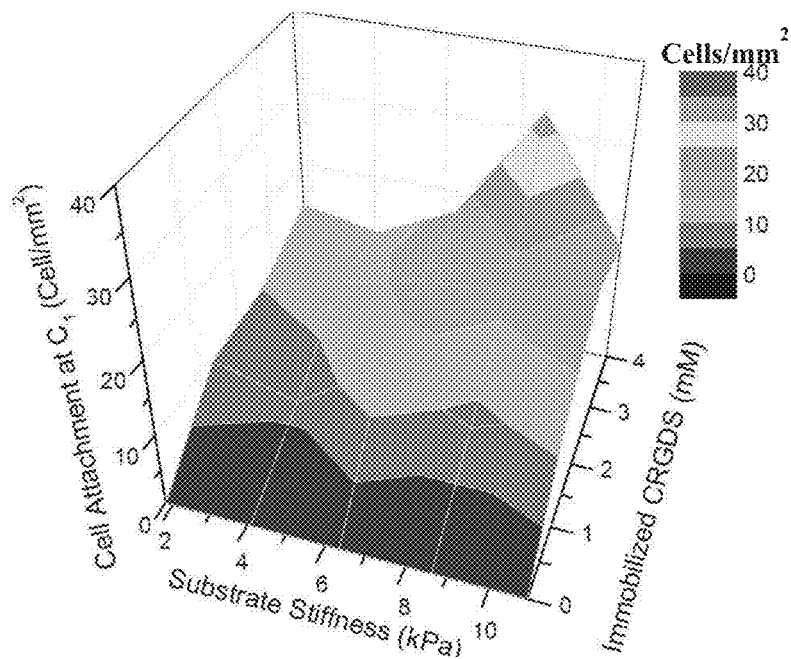
FIGS. 12-14 depict hMSC cell attachment, spreading and proliferation as analyzed in Example 3.
Figure 13:
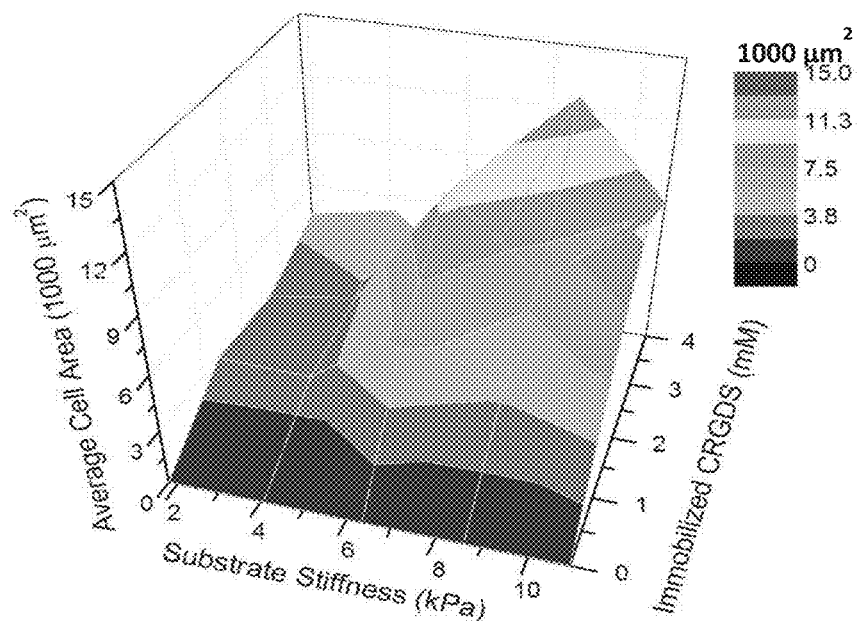
Figure 14:
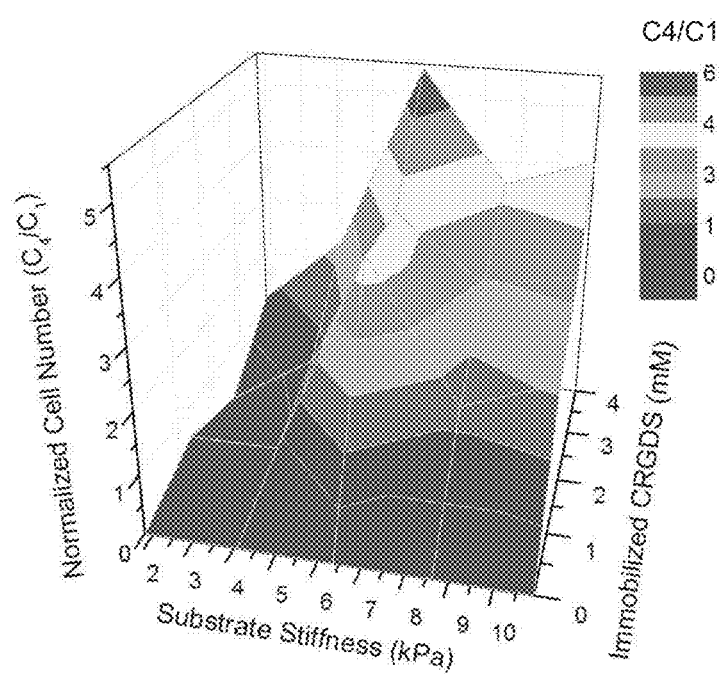

Increasing hydrogel spot stiffness (from 1.8 to 10.9 kPa) also resulted in increased hMSC initial cell attachment, spreading, and proliferation. Maximal hMSC initial cell attachment was seen on hydrogel spots of 8.2 kPa stiffness while maximal cell spreading and proliferation were both seen on hydrogel spots of 5.4 kPa stiffness. Results are shown in FIGS. 12-14.

Example 4

In this Example, hydrogel compositions of the present disclosure were prepared, human embryonic stem cells (hESCs) were cultured thereof, and cell expansion was analyzed.

Figure 15:
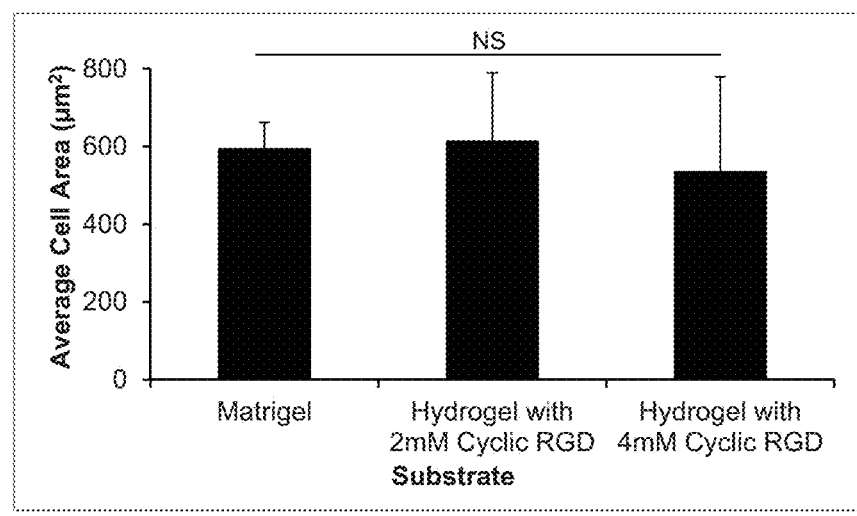
FIGS. 15 & 16 depict hESC cell spreading and proliferation rates as analyzed in Example 4.
Figure 16:
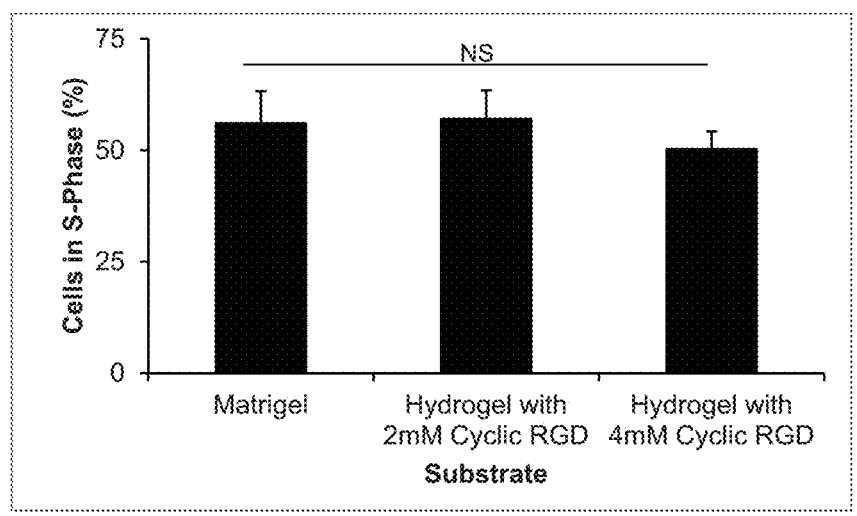

Hydrogel arrays containing hydrogel spots with stiffness values ranging from 1.8 to 10 kPa and varying immobilized cyclic RGD{Fd}C peptide (SEQ ID NO:33) concentrations from 0 to 4 mM. Note that total peptide concentration was maintained at 4 mM by supplementing the hydrogel precursor solution with a "scrambled", non-bioactive cyclic-RAD{d-Phe} peptide (SEQ ID NO:48). Following hydrogel array formation, H1 hESCs were seeded onto the hydrogel spots and cultured for up to 5 days. H1 hESCs cultured on hydrogels of 3-10 kPa stiffness and containing 2-4 mM cyclic-RGD{d-Phe} peptide exhibited cell spreading and proliferation rates similar to those cultured on MATRIGEL®-coated tissue culture polystyrene. Results are shown in FIGS. 15 & 16.

What is claimed is:

1. A method of promoting cellular expansion, the method comprising:
    preparing a hydrogel composition, wherein the hydrogel composition comprises an 8-arm, 20 kDa polyethylene glycol functionalized with norbornene, a crosslinking peptide, and a cell adhesion peptide;
    contacting a cell with the hydrogel composition; and
    culturing the cell.

2. The method of claim 1 wherein the cell is a circulating angiogenic cell.

3. The method of claim 2 wherein the hydrogel composition comprises at least 1 mM cell adhesion peptide selected from the group consisting of CRGDS (SEQ ID NO:2), Acetylated-GCYGRGDSPG (SEQ ID NO:31), cyclic RGD (SEQ ID NO:35), CRGD-$(G)_{13}$-PHSRN (SEQ ID NO:29), CPHSRN-$(SG)_5$-RGD (SEQ ID NO:30) and IKVAV (SEQ ID NO:38).

4. The method of claim 2 wherein the hydrogel composition comprises a shear modulus range of from about 2 kPa to about 12 kPa.

5. The method of claim 1 wherein the cell is a human mesenchymal stem cell.

6. The method of claim 5 wherein the hydrogel composition comprises a shear modulus of from about 1.8 kPa to about 33 kPa.

7. The method of claim 5 wherein the hydrogel composition comprises at least 0.25 mM of cell adhesion peptide selected from the group consisting of CRGDS (SEQ ID NO:2), Acetylated-GCYGRGDSPG (SEQ ID NO:31), cyclic RGD (SEQ ID NO:35), CRGD-(G)$_{13}$-PHSRN (SEQ ID NO:29), CPHSRN-(SG)$_5$-RGD (SEQ ID NO:30) and IKVAV (SEQ ID NO:38).

8. The method of claim 5 wherein the cell is a human pluripotent stem cell selected from the group consisting of a human embryonic stem cell and human induced pluripotent stem cell.

9. The method of claim 8 wherein the hydrogel composition comprises at least 0.25 mM of cell adhesion peptide selected from the group consisting of CRGDS (SEQ ID NO:2), Acetylated-GCYGRGDSPG (SEQ ID NO:31), cyclic RGD (SEQ ID NO:35), CRGD-(G)$_{13}$-PHSRN (SEQ ID NO:29), CPHSRN-(SG)$_5$-RGD (SEQ ID NO:30) and IKVAV (SEQ ID NO:38).

10. The method of claim 8 wherein the hydrogel composition comprises a shear modulus of from about 3 kPa to about 16 kPa.

11. The method of claim 8 wherein the hydrogel composition further comprises immobilized low molecular weight heparin.

12. A method of promoting cellular differentiation, the method comprising:
preparing a hydrogel composition, wherein the hydrogel composition comprises an 8-arm, 20 kDa polyethylene glycol functionalized with norbornene, a crosslinking peptide, and a cell adhesion peptide;
contacting a cell with the hydrogel composition; and
culturing the cell.

13. The method of claim 12 wherein the cell is a human mesenchymal stem cell.

14. The method of claim 13 wherein the hydrogel composition comprises a shear modulus of from about 1.8 kPa to about 33 kPa.

15. The method of claim 13 wherein the hydrogel composition comprises at least 0.25 mM of cell adhesion peptide selected from the group consisting of CRGDS (SEQ ID NO:2), Acetylated-GCYGRGDSPG (SEQ ID NO:31), cyclic RGD (SEQ ID NO:35), CRGD-(G)$_{13}$-PHSRN (SEQ ID NO:29), CPHSRN-(SG)$_5$-RGD (SEQ ID NO:30) and IKVAV (SEQ ID NO:38).

16. The method of claim 12 wherein the cell is a human pluripotent stem cell selected from the group consisting of a human embryonic stem cell and human induced pluripotent stem cell.

17. The method of claim 16 wherein the hydrogel composition comprises at least 0.25 mM of cell adhesion peptide selected from the group consisting of CRGDS (SEQ ID NO:2), Acetylated-GCYGRGDSPG (SEQ ID NO:31), cyclic RGD (SEQ ID NO:35), CRGD-(G)$_{13}$-PHSRN (SEQ ID NO:29), CPHSRN-(SG)$_5$-RGD (SEQ ID NO:30) and IKVAV (SEQ ID NO:38).

18. The method of claim 16 wherein the hydrogel composition comprises a shear modulus of from about 3 kPa to about 16 kPa.

19. A method of promoting cellular expansion, the method comprising:
preparing a hydrogel composition, wherein the hydrogel composition comprises a polyethylene glycol functionalized with norbornene, a crosslinking peptide, a cell adhesion peptide, and immobilized low molecular weight heparin;
contacting a cell with the hydrogel composition; and
culturing the cell.

* * * * *